United States Patent
Toumazou et al.

(10) Patent No.: US 9,283,323 B2
(45) Date of Patent: Mar. 15, 2016

(54) INSULIN PUMP

(75) Inventors: Christofer Toumazou, London (GB);
Pantelis Georgiou, Middlesex (GB);
Pau Herrero Vinas, London (GB);
Calvin Sim, Kowloon (HK)

(73) Assignee: GENE ONYX LIMITED, Road Town, Tortola (VG)

( * ) Notice: Subject to any disclaimer, the term of this patent is extended or adjusted under 35 U.S.C. 154(b) by 480 days.

(21) Appl. No.: 13/570,525

(22) Filed: Aug. 9, 2012

(65) Prior Publication Data

US 2013/0041343 A1    Feb. 14, 2013

(30) Foreign Application Priority Data

Aug. 12, 2011    (GB) .................................. 1113933.4

(51) Int. Cl.
| | |
|---|---|
| *A61M 31/00* | (2006.01) |
| *A61M 5/172* | (2006.01) |
| *G06F 19/00* | (2011.01) |
| *A61M 5/142* | (2006.01) |

(52) U.S. Cl.
CPC .............. *A61M 5/1723* (2013.01); *A61M 5/142* (2013.01); *G06F 19/3468* (2013.01); *A61M 2005/14208* (2013.01); *A61M 2005/1726* (2013.01); *A61M 2205/52* (2013.01); *A61M 2230/201* (2013.01)

(58) Field of Classification Search
CPC ............................ A61B 5/4839; A61M 5/1723
USPC .................... 604/66, 67, 504, 890.1
See application file for complete search history.

(56) References Cited

U.S. PATENT DOCUMENTS

| | | | |
|---|---|---|---|
| 2007/0173461 A1 | 7/2007 | Nakamura | |
| 2007/0173761 A1* | 7/2007 | Kanderian et al. | 604/131 |
| 2008/0146994 A1* | 6/2008 | Gerber | 604/66 |
| 2008/0183060 A1* | 7/2008 | Steil et al. | 600/365 |

FOREIGN PATENT DOCUMENTS

| | | |
|---|---|---|
| WO | 2008/048556 A2 | 4/2008 |
| WO | 2008/088490 A1 | 7/2008 |
| WO | 2009/009528 A2 | 1/2009 |

OTHER PUBLICATIONS

Steil et al., Diabetes Research and Clinical Practice, vol. 74, pp. S183-S186 (2006).
Search Report, dated Dec. 5, 2011, issued in priority Application No. GB 1113933.4.

(Continued)

*Primary Examiner* — Emily Schmidt
(74) *Attorney, Agent, or Firm* — Saul Ewing LLP

(57) ABSTRACT

The present invention relates to a controller unit and methods for controlling an insulin pump. The controller unit includes a user input that receives a gain factor. The gain factor has been calculated based on historical data in relation to a patient. The controller unit includes a measurement input for receiving data representative of a measured blood glucose level for the patient. Processing logic of the controller unit is configured to apply the measured blood glucose level to a pancreatic beta-cell insulin secretion computational model to predict an insulin output level, apply the gain factor to the predicted insulin output level to determine a patient insulin deficiency level, and calculate a control signal for controlling the insulin output level of the insulin pump based on the patient insulin deficiency level. Methods are provided for optimizing the gain factor based on the historical data in relation to the patient.

38 Claims, 10 Drawing Sheets

(56) References Cited

OTHER PUBLICATIONS

Hovorka R. Continuous glucose monitoring and closed-loop systems. Diab Med. 2006;23(1):1-12.

Kovatchev B, Anderson S, Heinemann L, Clarke W. Comparison of the numerical and clinical accuracy of four continuous glucose monitors. Diabetes Care. 2008;31(6):1160-1164.

Bequette BW. A critical assessment of algorithms and challenges in the development of a closed-loop artificial pancreas. Diabetes Technol Ther. 2005;7(1):28-47.

Rowe R. Insulin pump therapy. Diabet Medicine. 2001;18(Suppl 4):4-5.

Steil GM, Rebrin K, Darwin C, Hariri F, Saad MF. Feasibility of automating insulin delivery for the treatment of type 1 diabetes. Diabetes. 2006;55(12):3344-3350.

Hovorka R, Canonico V, Chassin LJ, Haueter U, Massi-Benedetti M, Orsini Federici M, Pieber TR, Schaller HC, Schaupp L, Vering T, Wilinska ME. Nonlinear model predictive control of glucose concentration in subjects with type 1 diabetes. Physiol Mea. 2004;25(4):905-920.

El-Khatib FH, Russell SJ, Nathan DM, Sutherlin RG, Damiano ER. A bihormonal closed-loop artificial pancreas for type 1 diabetes. Sci Transl Med. 2010;2(27) 27ra27.

Atlas E, Nimri R, Miller S, Grunberg EA, Phillip M. MD-logic artificial pancreas system: a pilot study in adults with type 1 diabetes. Diabetes Care. 2010;33(5):1072-1076.

Campos-Delgado DU, Hernández-Ordoñez M, Femat R, Gordillo-Moscoso A. Fuzzy-based controller for glucose regulation in type-1 diabetic patients by subcutaneous route. IEEE Trans Biomed Eng. 2006;53(11):2201-2210.

Mead C. Reading (MA): Addison-Wesley; 1989. Analog VLSI and neural systems (copy not available).

Georgiou J, Toumazou C. A 126-μW cochlear chip for a totally implantable system. IEEE J Solid State Circuit. 2005;40(2):430-443.

Degenaar P, Grossman N, Memon MA, Burrone J, Dawson M, Drakakis E, Neil M, Nikolic K. Optobionic vision—a new genetically enhanced light on retinal prosthesis. J Neural Eng. 2009;6(3)035007.

Constandinou TG, Georgiou J, Toumazou C. ISCAS 2009: IEEE International Symposium on Circuits and Systems. Taipei, Taiwan: May 27, 2009. A neural implant ASIC for the restoration of balance in individuals with vestibular dysfunction; pp. 641-644.

Caumo A, Luzi L. First-phase insulin secretion: does it exist in real life? Considerations on shape and function. Am J Physiol Endocrinol Metab. 2004;287(3):E371-85.

Steil GM, Panteleon AE, Rebrin K. Closed-loop insulin delivery—the path to physiological glucose control. Adv Drug Deily Rev. 2004;56(2):125-144.

Keenan DB, Mastrototaro JJ, Voskanyan G, Steil GM. Delays in minimally invasive continuous glucose monitoring devices: a review of current technology. J Diabetes Sci Technol. 2009;3(5):1207-1214.

Heinemann L. Variability of insulin absorption and insulin action. Diabetes Technol Ther.2002;4(5):673-682.

Steil GM, Rebrin K, Janowski R, Darwin C, Saad MF. Modeling beta-cell insulin secretion—implications for closed-loop glucose homeostasis. Diabetes Technol Ther. 2003;5(6):953-964.

Breda E, Toffolo G, Polonsky KS, Cobelli C. Insulin release in impaired glucose tolerance: oral minimal model predicts normal sensitivity to glucose but defective response times. Diabetes. 2002;51(Suppl 1):S227-33.

Oliver N, Georgiou P, Johnston D, Toumazou C. A benchtop closed-loop system controlled by a bio-inspired silicon implementation of the pancreatic beta cell. J Diabetes Sci Technol. 2009;3(6):1419-1424.

Pedersen MG, Bertram R, Sherman A. Intra- and inter-islet synchronization of metabolically driven insulin secretion. Biophys J. 2005;89(1):107-119.

Bertuzzi A, Salinari S, Mingrone G. Insulin granule trafficking in β-cells: mathematical model of glucose-induced insulin secretion. Am J Physiol Endocrinol Metab. 2007;293(1):E396-409.

Chen Y, Wang S, Sherman A. Identifying the targets of the amplifying pathway for insulin secretion in pancreatic β-cells by kinetic modeling of granule exocytosis. Biophysical J. 2008;95(5):2226-2241.

Pedersen MG, Toffolo GM, Cobelli C. Cellular modeling: insight into oral minimal models of insulin secretion. Am J Physiol Endocrinol Metab. 2010;298(3):E597-601.

Kovatchev BP, Breton M, Dalla Man C, Cobelli C. In silico preclinical trials: A proof of concept in closed-loop control of type 1 diabetes. J Diabetes Sci Technol. 2009;3(1):44-55.

Hovorka R, Chassin L, Luzio SD, Playle R, Owens DR. Pancreatic β-cell responsiveness during meal tolerance test: model assess-ment in normal subjects and subjects with newly diagnosed noninsulin-dependent diabetes mellitus. J Clin Endocrinol Metab. 1998;83(3):744-750.

Toffolo G, Breda E, Cavaghan MK, Ehrmann DA, Polonsky KS, Cobelli C. Quantitative indexes of β-cell function during graded up&down glucose infusion from C-peptide minimal models. Am J Physiol Endocrinol Metab. 2001;280(1):E2-10.

Cretti A, Lehtovirta M, Bonora E, Brunato B, Zenti MG, Tosi F, Caputo M, Caruso B, Groop LC, Muggeo M, Bonadonna RC. Assessment of β-cell function during the oral glucose tolerance test by a minimal model of insulin secretion. Eur J Clin Invest. 2001;31(5):405-416.

Mari A, Schmitz O, Gastaldelli A, Oestergaard T, Nyholm B, Ferrannini E. Meal and oral glucose tests for assessment of β-cell function: modeling analysis in normal subjects. Am J Physiol Endocrinol Metab. 2002;283(6):E1159-66.

Pedersen MG, Corradin A, Toffolo GM, Cobelli C. A subcellular model of glucose-stimulated pancreatic insulin secretion. Philos Transact A Math Phys Eng Sci. 2008;366(1880):3525-3543.

Grodsky GM. A threshold distribution hypothesis for packet storage of insulin and its mathematical modeling. J Clin Invest. 1972;51(8):2047-2059.

Dassau E, Bequette BW, Buckingham BA, Doyle FJ., 3rd Detection of a meal using continuous glucose monitoring: implications for an artificial β-cell. Diabetes Care. 2008;31(2):295-300.

Dassau E, Cameron F, Lee H, Bequette BW, Zisser H, Jovanovic L, Chase HP, Wilson DM, Buckingham BA, Doyle FJ., 3rd Real-time hypoglycemia prediction suite using continuous glucose monitoring: a safety net for the artificial pancreas. Diabetes Care. 2010;33(6):1249-1254.

Weinzimer SA, Steil GM, Swan KL, Dziura J, Kurtz N, Tamborlane WV. Fully automated closed-loop insulin delivery versus semiautomated hybrid control in pediatric patients with type 1 diabetes using an artificial pancreas. Diabetes Care. 2008;31(5):934-939.

Steil G, Rebrin K, Mastrototaro JJ. Metabolic modelling and the closed-loop insulin delivery problem. Diabetes Res Clin Pract. 2006;74(Suppl 2):S183-6.

Lee H, Buckingham BA, Wilson DM, Bequette BW. A closed loop artificial pancreas using model predictive control and a sliding meal size estimator. J Diabetes Sci Technol. 2009;3(5):1082-1090.

Clarke W, Kovatchev B. Statistical tools to analyze continuous glucose monitor data. Diabetes Technol Ther. 2009;11 (Suppl 1):S45-54.

Magni L, Raimondo DM, Dalla Man C, Breton M, Patek S, Nicolao GD, Cobelli C, Kovatchev BP. Evaluating the efficacy of closed-loop glucose regulation via control-variability grid analysis. J Diabetes Sci Technol. 2008;2(4):630-635.

Pedersen: "Cellular modeling: insight into oral minimal models of insulin secretion," Am J. Physiol. Endocrinol. Metab., vol. 298, pp. E597-E601 (Dec. 15, 2009).

Herrero Pau et al., "A bio-inspired glucose controller based on pancreatic [beta] -cell physiology," J. of Diabetes Science and Technology, US, vol. 6, No. 3, pp. 606-616 (Jan. 1, 2012).

International Search Report, dated Apr. 18, 2013, issued in related International Application No. PCT/EP2012/065725.

\* cited by examiner

INSULIN PUMP

TECHNICAL FIELD

The present invention relates to methods and apparatus for controlling an insulin pump. In particular, the present invention relates to a method and apparatus for controlling and optimising the performance of an insulin pump for each user.

BACKGROUND

Type 1 diabetes mellitus (T1DM) is a chronic metabolic disease characterized by T-cell-mediated autoimmune destruction of the insulin-secreting β-cells of the endocrine pancreas. Absolute insulin deficiency occurs, leading to hyperglycemia. Current regimens for treating type 1 diabetes in clinical practice are mainly based on injections of subcutaneous insulin either continuously or several times daily in dosages determined by intermittent measurements of blood glucose levels. The blood glucose level (or blood sugar concentration) comprises or represents the amount of glucose in the blood of an animal or human being and is measured in terms of molar concentration (mmol/L) according to the International Standard or mass concentration (mg/dL) according to the US Standard. The latter is used in the following description.

The Diabetes Control and Complications Trial (DCCT) Research Group published their results on the effect of intensive treatment of diabetes on the development and progression of long-term complications in insulin-dependent diabetes mellitus in New England Journal Medical, 1993, 329(14), pages 977-986, which demonstrated that intensive management using this treatment algorithm reduced micro-vascular complications by 50-76%. However, this was at the expense of increased time spent in hypoglycemia, especially at hemoglobin A1c levels <7.5%.

In other studies, intensive management resulted in subjects spending 30% of the day with glucose values >10 mM (180 mg/dl) and >2 hours/day in hypoglycemia, often at night as described by B. W. Bode, S. Schwartz, H. A. Stubbs, J. E. Block, "*Glycemic characteristics in continuously monitored patients with type 1 and type 2 diabetes: normative values*", Diabetes Care, 2005, 28(10), pages 2361-6. This led to automatic blood glucose control.

An automatic closed-loop system was described by R. Hovorka, "*Continuous glucose monitoring and closed loop systems.*" Diab Med., 2005, 23(1), pages 1-12, which provided the potential to improve hemoglobin A1c while avoiding hypoglycemia. Many researchers have found that this type of system requires continuous glucose measurement, a control device, and a pump for insulin delivery. See for example, B. Kovatchev, S. Anderson, L. Heinemann, and W. Clarke, "*Comparison of the numerical and clinical accuracy of four continuous glucose monitors*", Diabetes Care, 2008, 31, pages 1160-1164; B. W. Bequette, "*A critical assessment of algorithms and challenges in the development of a closed—loop artificial pancreas*", Diabetes Technol Ther., 2005, 7, page 28; or R. Rowe, "*Insulin pump therapy*", Diabetic Medicine, 2001, 18, pages 4-5.

Closed-loop control algorithms used in the context of an artificial pancreas (AP) have been mainly based on classical control engineering techniques, and dominated by Proportional Integral Derivative (PID) control as described by G. M. Steil, K. Rebrin, C. Darwin, F. Hariri and M. F. Saad, "*Feasibility of automating insulin delivery for the treatment of type 1 diabetes*", Diabetes, 2006, 55, pages 3344-3350, and Model Predictive Control (MPC) as in R. Hovorka, "*Continuous glucose monitoring and closed loop systems*", Diab Med., 2005, 23(1), pages 1-12, or F. H. El—Khatib, S. J. Russell, D. M. Nathan, R. G. Sutherlin, and E. R. Damiano, "*A bihormonal closed—loop artificial pancreas for type 1 diabetes*", Sci Transl Med., 2010, 2(27), page 27.

Other approaches, based on empiric knowledge, have also been proposed through the use of artificial intelligence techniques as described in E. Atlas, R. Nimri, S. Miller, E. A. Grunberg and M. Phillip, "*MD-Logic Artificial Pancreas System—A pilot study in adults with type 1 diabetes*", Diabetes Care, 2010, 33(5), pages 1072-1076 and D. Campos-Delgado, M. Hernandez-Ordonez, R. Fermat, and A. Gordillo-Moscoso, "*Fuzzy-based controller for glucose regulation in type-1 diabetic patients by subcutaneous route*", IEEE Trans Biomed Eng., 2006, 53(11), pages 2201-2210.

Bio-inspired approaches for solving medical problems have been motivated by the belief that nature has evolved over millions of years to carry out its tasks more optimally and efficiently. Therefore replicating the functionality of the human body can lead to a system with greater physiological function, which the body can accept. Bio-inspired technologies for artificial organs have already been successfully implemented in different medical areas including cochlear implants, retinal implants, and vestibular implants. C. Toumazou, J. A. Georgiou, "*A 126 µW cochlear chip for a totally implantable system*"; IEEE Journal Solid State Circuits, 2005, 40(2), pages 430-43 describes modelling the way the basilar membrane of the cochlear behaves and therefore can restore hearing. P. Degenaar, N. Grossman, M. A. Memon, et al, "*Optobionic vision—a new genetically enhanced light on retinal prosthesis*"; J Neural Eng., 2009, 6, pages 1741-2552, describe retinal implants that model the local processing which occurs in the neuronal circuits of the retina to derive extremely fast and low power image restoration. Constandinou, T. G., Georgiou, J., Toumazou, C., "*A neural implant ASIC for the restoration of balance in individuals with vestibular dysfunction*", Circuits and Systems, 2009, ISCAS 2009. IEEE International Symposium on, pages 641-644, 24-27 May 2009 presented vestibular implants that replicate the inertial measurements of the human body to restore balance. Given these successes, it has been considered there may be some benefit to consider a control strategy for controlling blood glucose based on the biological function of the pancreas.

Bio-inspired control systems can be used to replicate the functionality of the pancreas and provide more physiological solutions, especially in the area of prosthetic organs. The bio-inspired approaches for blood glucose control is based on the biphasic nature of insulin secretion from the beta-cells in the pancreas, which depends on the type and magnitude of the glucose stimulus as described by A. Caumo and L. Luzi, "*First-phase insulin secretion: does it exist in real life? Considerations on shape and function*"; AJP—End., 2004, 287 (3), E371-E385. Both animal and human studies indicate that the first-phase insulin response to intravenous glucose has beneficial effects on the regulation of glucose metabolism. In particular, the first-phase has a profound and long-term inhibitory effect on hepatic glucose production. Likewise, the early insulin response to ingested glucose is an important determinant of prandial glucose tolerance.

FIG. 1 is an illustration of a graph showing an example of biphasic insulin secretion by a β-cell corresponding to a glucose stimulus from a meal. The y-axis of the upper graph represents plasma glucose (mg/dL) and the y-axis of the lower graph represents insulin secretion (ug/min), where the x-axis on both graphs represents time in minutes. The graphs illustrate the presence of a sharp first-phase due to the rapidly changing glucose concentration (i.e. derivative effect) and afterwards, a second-phase represented by sustained insulin release. Replicating the β-cell behaviour in response to a glucose stimulus may assist in controlling blood glucose concentration in T1DM subjects.

G. M. Steil et. al., "*Modeling b-Cell Insulin Secretion-Implications for Closed-Loop Glucose Homeostasis*", Diabetes Technology & Therapeutics, 2003, 5(6) describes using a bio-inspired approach for blood glucose control, which used a minimal model of insulin secretion, previously described by E. Breda et. al, "*Insulin release in impaired glucose tolerance: oral minimal model predicts normal sensitivity to glucose but defective response times*"; Diabetes, 2002, 51(1), S227-S233.

This simple model represents the insulin secretion by decomposing it into a static rate of secretion, which basically depends on the plasma glucose concentration, and a dynamic secretion rate (second phase), which depends on the rate of change of plasma glucose concentration (first phase). Steil et. al. compared the minimal model of insulin secretion with a PID controller and concluded that both were able to fit experimental data. However, the insulin secretion model was less stable than the PID controller under closed-loop conditions due to the simplification of the bio-inspired model.

Oliver et al., "*A Benchtop Closed-Loop System Controlled by a Bio-Inspired Silicon Implementation of the Pancreatic β-Cell*", Journal of Diabetes Science and Technology, 2009, 3(6), used a model of the electrical activity of β-cell for closed-loop glucose control and implemented a semiconductor ASIC, which formed a "silicon" beta cell. However, the model lacked sufficient detail of insulin release.

Some recent developments of mathematical models of β-cell physiology are described by M. G. Pedersen et. al., "*Intra-and inter-islet synchronization of metabolically driven insulin secretion*"; Biophys J., 2005, 89(1), pages 107-119; A. Bertuzzi et. al., "*Insulin granule trafficking in beta-cells: mathematical model of glucose-induced insulin secretion*"; Am J Physiol Endocrinol Metab., 2007, 293, E396-E409; Yi-der Chen et. al., "*Identifying the Targets of the Amplifying Pathway for Insulin Secretion in Pancreatic β-Cells by Kinetic Modelling of Granule Exocytosis*", Biophysical Journal, 2008, 95(5), pages 2226-2241, and M. G. Pedersen et. al., "*Cellular modeling: insight into oral minimal models of insulin secretion*", Am J Physiol Endocrinol Metab., 2010, 298, E597-E601. These documents describe the glucose-induced insulin release at a molecular level and have led to a new class of bio-inspired glucose control algorithms.

However, currently available technologies for continuous glucose monitoring (CGM) and continuous insulin infusion (CSII) use the subcutaneous (s.c.) route, which despite the clear advantage of being minimally invasive, are far from being physiological, and consequently non-optimal. The s.c. route introduces some extra difficulties to the glucose control in the form of time delays in the glucose sensing and insulin action, measurement errors and higher variability. Time delays are introduced by glucose sensing (up to 15 minutes) and insulin action (15-20 minutes). The variability of these delays can be high and the accuracy of the current s.c. continuous glucose sensors are far from being optimal with mean absolute differences of up to 20%, especially in hypoglycaemia, which is the critical state to avoid. It is desirable to devise an improved control strategy for controlling insulin pumps that overcomes these limitations.

SUMMARY

It is an object of the present invention to provide apparatus and methods for controlling an insulin pump based on bio-inspired insulin secretion computational models for use in optimising insulin delivery to each user or patient.

According to a first aspect of the invention there is provided an apparatus for controlling an insulin pump, the apparatus including a user input, a measurement input, and processing logic connected together. The user input for receiving a gain factor, the gain factor having been calculated based on historical data in relation to a patient. The measurement input for receiving data representative of a measured blood glucose level for the patient. The processing logic configured to apply the measured blood glucose level to an insulin secretion computational model to predict an insulin output level, apply the gain factor to the predicted insulin output level to determine a patient insulin deficiency level, and calculate a control signal for controlling the insulin output level of the insulin pump based on the patient insulin deficiency level.

As an option, the invention further provides applying the gain factor to the predicted insulin output level for a first period of time after ingestion of a meal by the patient Optionally, the invention further includes the user input receiving second and third gain factors, the second and third gain factors having been calculated based on the historical data in relation to the patient. The processing logic being configured to apply the second gain factor to the predicted insulin output level when the blood glucose level for the patient is equal to or above a predetermined glucose threshold, and apply the third gain factor to the predicted insulin output level when the first period of time expires and when the blood glucose level for the patient is below the predetermined glucose threshold. As an option, the insulin secretion computational model is a pancreatic beta-cell computational model and/or the measured blood glucose level is measured from a blood glucose sensor from the group of a subcutaneous blood glucose sensor, intravenous blood glucose sensor, and a non-invasive blood glucose sensor. The apparatus is provided as an integrated circuit.

According to second aspect of the invention there is provided an insulin system for use by a patient comprising an insulin pump for the patient, a blood glucose sensor for the patient, and an apparatus as described for use in controlling the insulin output level of the insulin pump, the apparatus connected to the insulin pump and the blood glucose sensor. As an option, the blood glucose sensor is a sensor from the group of a subcutaneous blood glucose sensor, intravenous blood glucose sensor, and a non-invasive blood glucose sensor.

According to a third aspect of the invention there is provided an insulin pump comprising an apparatus as described for controlling the output insulin level of a pump unit of the insulin pump.

According to a fourth aspect of the invention there is provided a method for controlling an insulin pump, the method comprising receiving a gain factor, the gain factor having been calculated based on historical data in relation to a patient, receiving data representative of a measured blood glucose level for the patient, applying the measured blood glucose level to an insulin secretion computational model to predict an insulin output level, applying the gain factor to the predicted insulin output level to determine a patient insulin deficiency level, and calculating a control signal for controlling the insulin output level of the insulin pump based on the patient insulin deficiency level.

As an option, the invention further provides the steps of applying the gain factor to the predicted insulin output level for a first period of time after ingestion of a meal by the patient. Optionally, receiving second and third gain factors, the second and third gain factors having been calculated based on the historical data in relation to the patient, and applying the second gain factor to the predicted insulin output level when the blood glucose level for the patient is equal to or above a predetermined glucose threshold, and applying the third gain factor to the predicted insulin output level when the first period of time expires and when the blood glucose level for the patient is below the predetermined glucose threshold. As an option, the insulin secretion computational model is a pancreatic beta-cell computational model and/or the measured blood glucose level is measured from a blood glucose sensor from the group of a subcutaneous blood glucose sensor, intravenous blood glucose sensor, and a non-invasive blood glucose sensor.

According to a fifth aspect of the invention there is provided a method of controlling blood glucose levels within a patient, including calculating a gain factor for the patient based upon historical data in relation to the patient, measuring a blood glucose level in the patient, applying the measured blood glucose level to an insulin secretion computational model to predict an insulin output level, calculating a patient insulin deficiency level based on said gain factor and the predicted insulin output level, and using the patient insulin deficiency level as a control input for an insulin pump configured to pump insulin into the patient. As an option, the insulin secretion computational model is a pancreatic beta-cell computational model and/or the measured blood glucose level is measured from a blood glucose sensor from the group of a subcutaneous blood glucose sensor, intravenous blood glucose sensor, and a non-invasive blood glucose sensor.

According to another aspect of the invention there is provided a method of determining one or more gain factors for use in controlling an apparatus as described, including calculating one or more gain factors based upon historical data in relation to a patient and entering the one or more gain factors via the user input of the apparatus.

Optionally, the invention includes further calculating a first gain factor for a first period of time after ingestion of a meal by the patient. In addition, the invention further includes calculating a second gain factor for when the blood glucose level for the patient is equal to or above a predetermined glucose threshold, and calculating a third gain factor for when the first period of time expires and when the blood glucose level for the patient is below the predetermined glucose threshold. Optionally, the insulin secretion computational model is a pancreatic beta-cell computational model, the gain factors are calculated based on historical measured blood glucose levels for the patient. As an option, the historical measured blood glucose levels are measured subcutaneous blood glucose levels.

Optionally, at least one of the gain factors is calculated by minimising a predicted insulin output level cost function based on the historical data over a predetermined period of time for a given glucose profile. The predicted insulin output level cost function (J) is defined by $$J = \int_0^T U(t)\,dt - \left( \int_0^T SR_b(t)\,dt + \frac{CHO}{ICR} \right),$$

where T is the predetermined period of time, U(t) is the patient insulin deficiency level for calculating the control signal for controlling the insulin output level of the insulin pump, $SR_b(t)$ is the basal insulin rate, CHO is the amount of ingested carbohydrate, and ICR is the calculated insulin-to-carbohydrate ratio, which are adapted or derived from the historical data for the given glucose profile.

Further aspects of the invention provide a computer readable medium comprising computer instructions, which when executed on a processor or by processing logic, performs the methods according to the invention.

BRIEF DESCRIPTION OF THE DRAWINGS

In order that the invention may be more fully understood, some of the embodiments of the invention will now be described, by way of example only, with reference to the accompanying drawings, in which:

FIG. 6 illustrates example graphs of the operation of the apparatus of FIG. 5a.

DETAILED DESCRIPTION

In order to at least partially overcome the problems described above, it is proposed herein to incorporate bio-inspired models of insulin secretion of the pancreas to optimise the control of an insulin pump for each user or patient. In particular, the present invention provides a glucose controller unit based on a pancreatic B-cell computational model.

Figure 1:
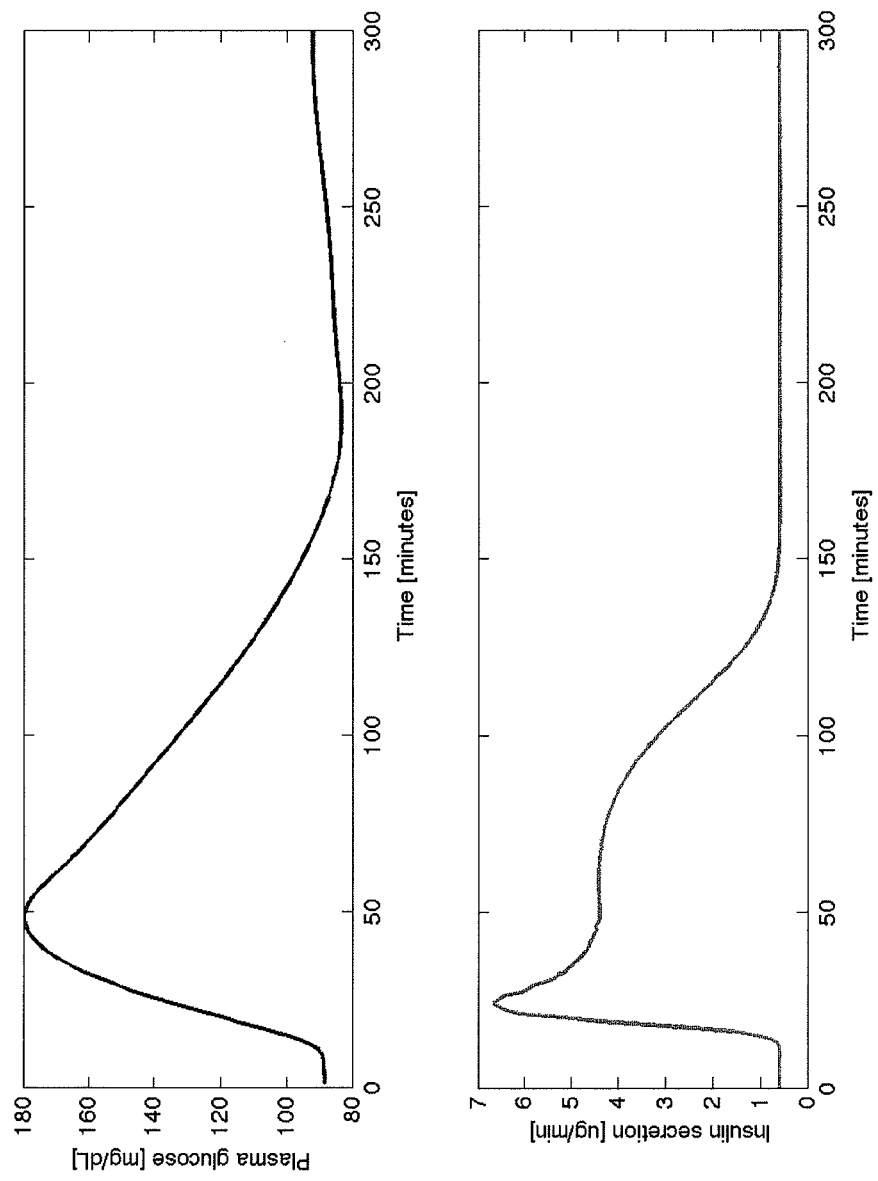
FIG. 1 illustrates example graphs of biphasic insulin secretion by a 13-cell.
Figure 2A:
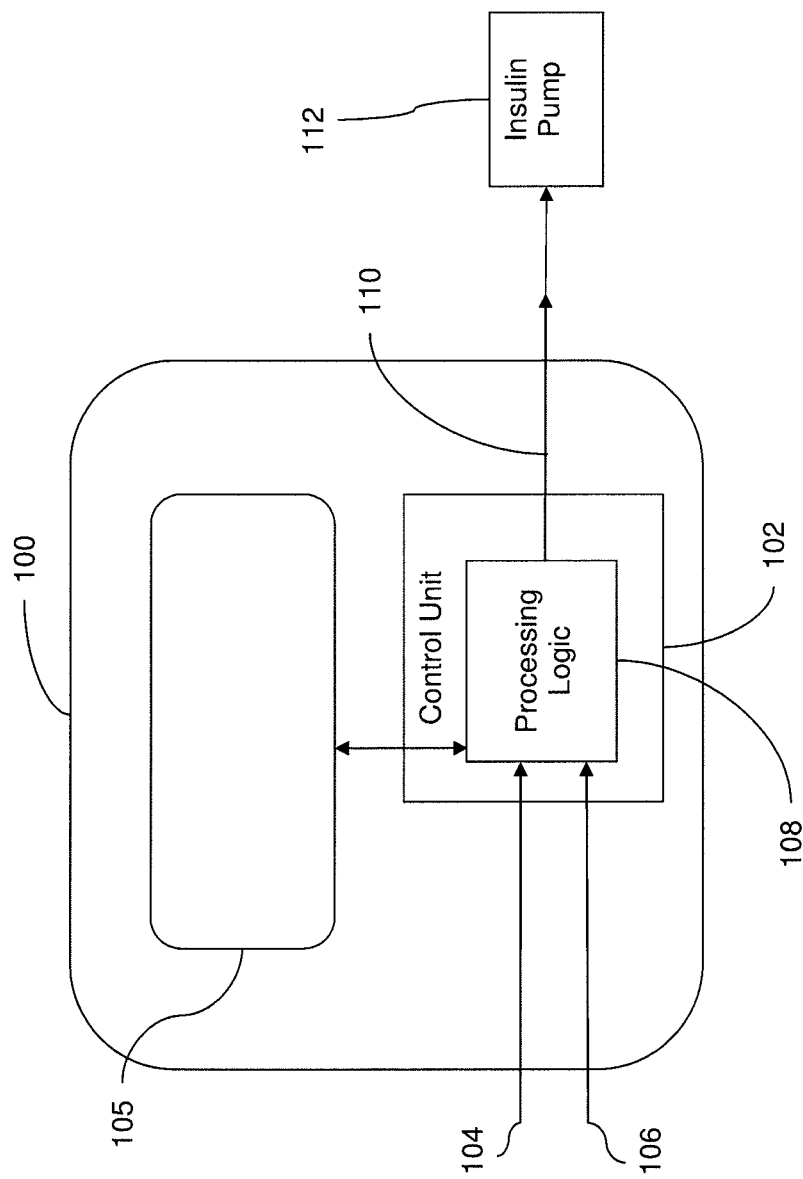
FIG. 2a illustrates schematically a control device including an apparatus according to the invention.

FIG. 2a illustrates an example of an control device 100 including a controller unit 102 for controlling the output of insulin pump 112. The controller unit 102 includes a user input 104, a measurement input 106, and processing logic 108. The controller unit 102 generates a control signal 110 that is input to insulin pump 112, the control signal 110 controls the insulin level provided by insulin pump 112 to a patient or user. The user input 104 receives one or more gain factors and other data for use by controller unit 102.

Figure 2B:
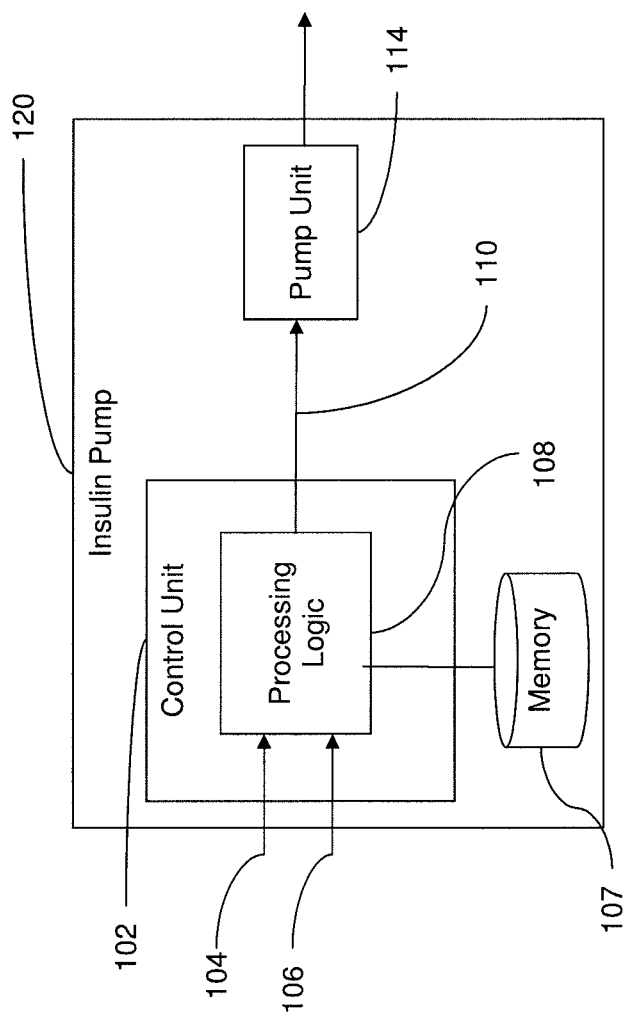
FIG. 2b illustrates schematically an insulin pump including an apparatus according to the invention.

FIG. 2b illustrates an example of an insulin pump 120 including the controller unit 102 for controlling the output of a pump unit 114 of the insulin pump 120, a memory unit 107 is included for storing one or more gain factors and other data for use by controller unit 102 and pump unit 112. The controller unit 102 includes the user input 104, the measurement input 106, and processing logic 108. The controller unit 102 generates a control signal 110 that is input to a pump unit 114, the control signal 110 controls the insulin level provided by pump unit 112 to a patient or user.

Referring to both FIGS. 2a and 2b, in operation, the user input 104 receives one or more gain factors, which have been determined based on historical data related to the patient or user. The gain factors are optimised based on the historical data of the patient or user and their insulin requirement. The historical data could be based on measured blood glucose or insulin levels, time of day, types of meals or snacks and other characteristics or parameters useful for characterising the user and their insulin requirements. Alternatively or in addition to, the controller device 100 or the controller unit 102 may include storage or memory for storing the one or more gain factors. As an example, in FIG. 2b, the gain factors may be stored in memory unit 107 and accessed by processing logic 108 when required.

The measurement input 106 receives data representative of a measured blood glucose level for the user or patient. The measurement input 106 may receive the measured blood glucose level from, by way of example, a subcutaneous blood glucose sensor (not shown) for the user or patient, an intravenous blood glucose sensor (not shown), an external blood glucose sensor (not shown), or a non-invasive blood glucose sensor (not shown) or other techniques for measuring the blood glucose level of the patient. As an example, non-invasive sensing techniques may include electro-optical technology that can perform non-invasive blood measurements by means of a finger probe, which can be used to measure blood glucose levels. Alternatively, a measured blood glucose level may be taken from a sample of the user or patient using finger or needle-stick prick methods, and entered manually, or automatically from a connection to the blood glucose level measuring device. The blood glucose levels can be measured at regular intervals or in real time.

The processing logic 108 may be configured to set a gain factor based on the one or more gain factors stored in memory unit 107. The gain factor could be selected from the one or more gain factors, the selection depending on the time of day or whether the user or patient is about to have or has ingested a meal or snack and other behaviour of the user or patient that affects their requirement of insulin. The processing logic 108 estimates a user or patient insulin deficiency level based on the gain factor, the measured blood glucose level for the patient, and a insulin secretion computational model. From the output of the model and use of the gain factor, the processing logic generates a control signal 110 for controlling the insulin output level of the insulin pump 112 of FIG. 2a or the pump unit 114 of the insulin pump 120 of FIG. 2b. The control signal 110 is generated based on the estimated patient insulin deficiency level. The patient insulin deficiency level is the additional insulin requirement that the user or patient requires from the insulin pump.

In particular, the processing logic 108 applies the measured blood glucose level to an insulin secretion computational model to predict an insulin output level. Preferably, the insulin secretion computational model is a pancreatic beta-cell computational model. The processing logic 108 applies the gain factor (or the selected gain factor) to the predicted insulin output level to determine a patient insulin deficiency level. The measurement input 106 receives data representative of a measured blood glucose level of the user or patient. Alternatively, a measured concentration or level of blood glucose of the user or patient could be measured non-invasively or via a needle-stick or other device for measuring blood glucose. The processing logic 108 calculates the control signal 110 for controlling the insulin output level of the insulin pump 112 or the insulin output level of pump unit 114 based on the patient insulin deficiency level.

The insulin secretion computational model may require further model parameters that can be tuned or calculated by optimising the computational model with the historical data of the patient. In addition to the gain factor(s) received by user input, the user input 104 may be further configured to receive tuned model parameters and other parameters for use by processing logic 108, which are applied to the insulin secretion computational model. The user input 104 can be further configured to also receive the insulin secretion computational model, which can be uploaded to processing logic 108 for use in calculating the control signal 110. This means that controller unit 102 can be updated with upgraded or new insulin secretion models or the computational insulin secretion model can be more customised to the users or patients requirements. The pancreatic beta-cell computational model and its model parameters, which can be tuned, is described with reference to FIGS. 3 to 6.

There may be a range of gain factors for processing logic 108 to select from for optimising the control of the output of insulin pump 112 or pump unit 114. The various gain factors may depend on the user or patient's blood glucose requirements and other factors such as the time of day or user behaviour regarding snacks or meals etc. Although there may be a plurality of gain factors or a plurality of sets of gain factors for different scenarios or users, by way of example and for simplicity, it is assumed that there are three gain factors, (a first, second and third gain factor), that are used to optimise the control of the insulin output level of insulin pump 100.

Processing logic 108 is configured to apply the gain factor (first gain factor) to the predicted insulin output level for a first period of time after ingestion of a meal by the patient. The user input can receive the second and third gain factors, the second and third gain factors having been calculated based on the historical data in relation to the patient. The processing logic 108 is further configured apply the second gain factor to the predicted insulin output level when the blood glucose level for the patient is equal to or above a predetermined glucose threshold, and apply the third gain factor to the predicted insulin output level when the first period of time expires and when the blood glucose level for the patient is below the predetermined glucose threshold.

Alternatively or in addition to, the processing logic 108 can be configured to set the gain factor to a first gain factor for a first period of time after ingestion of a meal by the patient or user. The patient or user may use the user input 104 to provide an indication that the user may ingest a meal or has ingested a meal. The second gain factor may be set by processing logic 108 when the blood glucose level for the patient or user is equal to or above a predetermined glucose threshold. The third gain factor may be set by processing logic 108 when the first period of time expires and when the blood glucose level for the patient is below the predetermined glucose threshold. The predetermined glucose threshold is determined based on the historical data and the patient's insulin requirements. The user input 104 may be configured to further receive the predetermined glucose threshold, or a set of predetermined glucose thresholds for use depending, among other things, on the patient's behaviour sleeping, working, or exercising, time of day, size of meal or snack and the glucose requirements.

Although the user of the insulin pump 112 or 120 may input several gain factors, as indicated above, at least three gain factors may be needed. To simplify this process, at least some of the gain factors could be derived from other gain factors input by the user. For example, the second and third gain factors could be calculated by processing logic 108 to be proportional to the first gain factor. The proportion depending on user requirements and/or optimising the control of insulin pump 100. As an example, the second gain factor may be set to be substantially half the proportion of the first gain factor, and the third gain factor may be set to substantially one fifth the proportion of the first gain factor. This means only the first gain factor needs to be entered by a user or patient of the insulin pump 100. It is to be appreciated, that there may be a set of first gain factors that are used depending on the user requirements or behaviour.

The controller unit 102 may include further logic or inputs for use in optimising the control of the output insulin provided by pump unit 112 to the user or patient. The processing logic 108 can be further configured to include logic for determining a first insulin level based on the measured concentration level of subcutaneous blood glucose for the patient and a received signal or user input 104 indicating ingestion of a meal. The patient insulin deficiency level may further include the first insulin level. The generation or calculation of the control signal 110 to insulin pump 112 or pump unit 114 is based the patient insulin deficiency level. As an example, the first insulin level may be calculated by a partial bolus calculator that calculates a bolus insulin level for the patient or user prior to or when the patient or user ingests a meal or snack.

The user input 104 may be configured to receive an indication of a meal to be ingested and the processing logic 108 applies the indication to the insulin secretion computational model to predict the insulin output level for the patient. The processing logic 108 can then calculate a pre-meal insulin level (or first insulin level) based on the measured blood glucose level and the indication of a meal to be ingested. The patient insulin deficiency level is further adjusted to include the pre-meal insulin level, such that the control signal 110 is generating using the pre-meal insulin level. The indication of a meal to be ingested may further include data representative of the amount of carbohydrates of the meal to be ingested. This assists the calculation of the pre-meal insulin level.

Alternatively or in addition to the first insulin level, the processing logic further includes logic for determining a second insulin level based on estimating the plasma insulin concentration from the insulin output level of the pump unit 112 or insulin pump 100. The patient insulin deficiency level further includes the second insulin level such that the generation or calculation of the control signal 110 is further based on the second insulin level. Alternatively, the processing logic 108 calculates a feedback insulin level (second insulin output) based on estimating a plasma insulin concentration from the insulin output level of the insulin pump 112 or 120. The patient insulin deficiency level is adjusted based on the feedback insulin level, such that the control signal 110 is calculated using the feedback insulin level. Alternatively or in addition to the first and second insulin levels (or pre-meal and feedback insulin levels), a third insulin level (or basal insulin level) based on a basal or minimum insulin profile of the user or patient may be used to adjust the patient insulin deficiency level for generating or calculating the control signal 110. The patient insulin deficiency level may be calculated by combining or summing gain factored predicted insulin output level, the patient pre-meal insulin level, the feedback insulin levels, and the basal insulin level. Further examples of calculating the patient insulin deficiency level used to generate and calculate the control signal 110 are provided with reference to FIGS. 2a to 6. Once the control signal 110 is calculated or generated, it is then sent to the insulin pump 112. Control signal 110 may be transmitted wirelessly to the insulin pump 112 or through wired media to insulin pump 112.

Figure 2C:
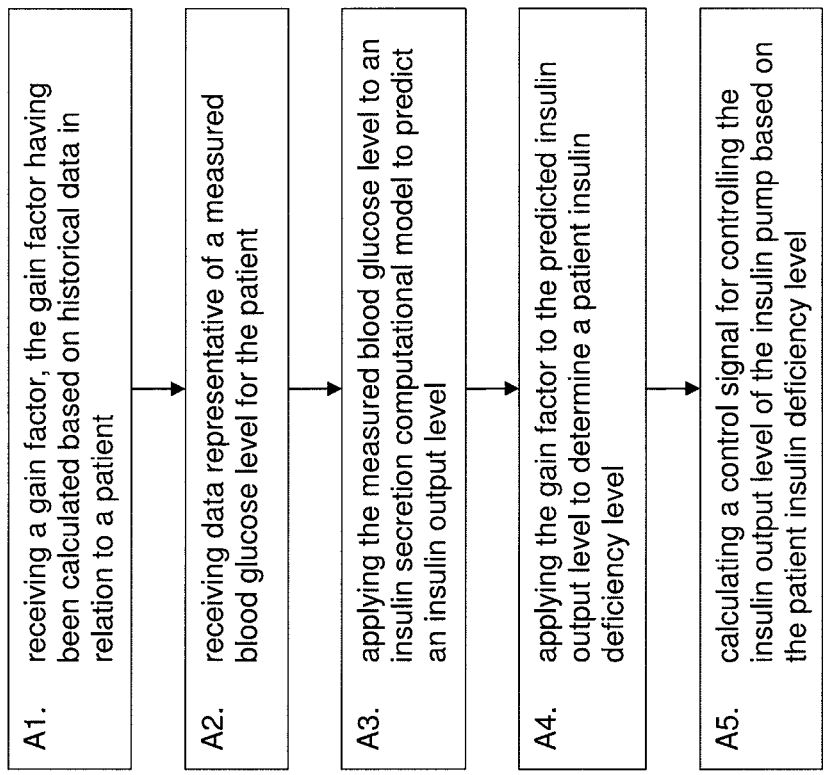
FIG. 2c illustrates a flow diagram of a process according to the invention.

FIG. 2c is a flow diagram illustrating a method of controlling an insulin pump 100. As described with reference to FIGS. 2a and 2b, the control device 100 and insulin pump 120 include a user input 104, a measurement input 106, and a control signal 110 for use in controlling the output insulin level of insulin pump 112 and pump unit 114, respectively. The method for controlling the insulin pump 120 or pump unit 114 is outlined by the following steps:

A1. Receiving a gain factor, the gain factor having been calculated based on historical data in relation to a patient.

A2. Receiving data representative of a measured blood glucose level for the patient.

A3. Applying the measured blood glucose level to an insulin secretion computational model to predict an insulin output level.

A4. Applying the gain factor to the predicted insulin output level to determine a patient insulin deficiency level.

A5. Calculating a control signal 110 for controlling the insulin output level of the insulin pump 112 or 120 based on the patient insulin deficiency level.

Figure 2D:
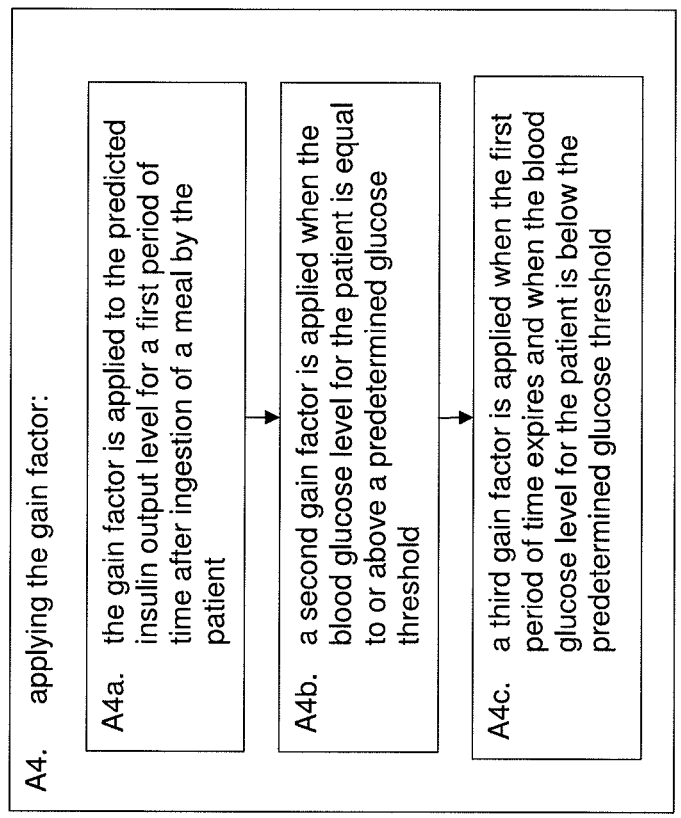
FIG. 2d illustrates a flow diagram for inclusion in the process according to the invention.

FIG. 2d is a flow diagram illustrating step A4 when the gain factor is applied to the predicted insulin output level, which optimises the control of insulin pump 112 and 120. Setting or applying the gain factor is as follows:

A4a. the gain factor (or first gain factor) is applied to the predicted insulin output level for a first period of time after ingestion of a meal by the patient.

A4b. a second gain factor is applied when the blood glucose level for the patient is equal to or above a predetermined glucose threshold.

A4c. a third gain factor is applied when the first period of time expires and when the blood glucose level for the patient is below the predetermined glucose threshold.

Optionally, second and third gain factors are received via user input 104, in which the second and third gain factors have been calculated based on the historical data in relation to the patient. Alternatively, the second and third gain factors are set or calculated to be proportional to the first gain factor. The second gain factor may be set to substantially half the proportion of the first gain factor, and the third gain factor may be set to substantially one fifth the proportion of the first gain factor. Alternatively or in addition to setting the gain factor, setting the gain factor includes selecting the gain factor from a set of gain factors determined from a set of specific glucose profiles based on the historical data.

The method may further include receiving tuned model parameters, which may be calculated by optimising the insulin computational model with the historical data of the patient and other parameters. Applying the tuned model parameters to the insulin secretion computational model. In addition, the method can include receiving data representative of the insulin secretion computational model, which can be uploaded to processing logic 108 for use in calculating the control signal 110. This means that controller unit 102 can be updated with upgraded or new insulin secretion models or the computational insulin secretion model can be further adjusted to the users or patients requirements.

The method of FIG. 2c may further include receiving an indication of a meal to be ingested, where the step A3 of applying the measured blood glucose level further includes applying the indication to the insulin secretion computational model to predict the insulin output level for the patient. Optionally, the method includes determining a first insulin level based on the measured blood glucose level for the patient and a received signal indicating ingestion of a meal, where calculating the control signal 110 is further based on the first insulin level. Alternatively or in addition to, the method further calculates a pre-meal insulin level (first insulin level) based on the measured blood glucose level and the indication of a meal to be ingested. The patient insulin deficiency level is further adjusted based on the pre-meal insulin level. From this, calculating the control signal 110 using the pre-meal insulin level can be performed. In addition, the indication of a meal to be ingested can further include data representative of the amount of carbohydrates of the meal to be ingested.

Alternatively or in addition to determining the first insulin level, the method may include determining a second insulin level based on estimating the plasma insulin concentration from the insulin output level of the insulin pump 110 or pump unit 112. The patient insulin deficiency level is further adjusted based on the second insulin level, where calculating the control signal 110 is further based on the second insulin level. That is, the method further includes calculating a feedback insulin level (second insulin level) based on estimating a plasma insulin concentration from the insulin output level of the insulin pump 112 or 120 or from the control signal 110 itself, and re-calculating the patient insulin deficiency level and control signal 110 using the feedback insulin level.

In order to use one or more gain factors in controlling the insulin pump 110, they need to be determined in relation to a patient or user of the insulin pump 110. Determining one or more gain factors is based on generating the one or more gain factors based upon historical data in relation to the patient. The gain factors are then entered by the user input 104 of the controller unit 102 or insulin pump 110. Determining the one or more gain factors includes determining a first gain factor for a first period of time after ingestion of a meal by the patient, a second gain factor for when a measured blood glucose level for the patient is equal to or above a predetermined threshold, and a third gain factor for when the first period of time expires and when the measured blood glucose level for the patient is below the predetermined threshold. The second gain factor can be set to substantially half the proportion of the first gain factor, and the third gain factor can be set to substantially one fifth the proportion of the first gain factor.

The gain factor or the first gain factor can be determined by minimising a predicted insulin output level cost function based on the historical data over a predetermined period of time for a given glucose profile. The predicted insulin output level cost function (J) may be defined by:

$$J = \int_0^T U(t)\,dt - \left( \int_0^T SR_b(t)\,dt + \frac{CHO}{ICR} \right),$$

where T is the predetermined period of time, U(t) is the patient insulin deficiency level for calculating the control signal 110 for controlling the insulin output level of the insulin pump, $SR_b(t)$ is the minimum insulin rate, CHO is the amount of ingested carbohydrate, and ICR is the calculated insulin-to-carbohydrate ratio, which are adapted or derived from the historical data for the given glucose profile. The first gain factor may be substantially in the range of [0,3). A set of gain factors may be determined from a set of specific glucose profiles based on the historical data of a patient. The control signal 110 is calculated from the patient insulin deficiency level which includes a combination of summation of the gain factored predicted insulin output level, the patient pre-meal insulin level, the feedback insulin levels, and the basal insulin level. Further examples of calculating the patient insulin deficiency level and control signal 110 are provided with reference to FIGS. 2a to 6.

As mentioned above, the processing logic 108 uses an insulin secretion computational model based on a pancreatic beta-cell to provide the predicted insulin level based on the data received at the measurement input 106. There are many bio-inspired computational models that can be used to estimate or predict a patient's or user's insulin levels. Existing glucose-stimulated pancreatic insulin secretion models include minimal models as described by Hovorka et. al., "*Pancreatic beta-cell responsiveness during meal tolerance test: model assessment in normal subjects and subjects with newly diagnosed noninsulin-dependent diabetes mellitus*", J Clin Endocrinol Metab, 1998, 83(3), pages 744-750; Toffolo et. al, "*Quantitative indexes of beta-cell function during graded up & down glucose infusion from c-peptide minimal models*", Am J Physiol Endocrinol Metab, 2001, 280(1), E210; A. Cretti et. al, "*Assessment of beta-cell function during the oral glucose tolerance test by a minimal model of insulin secretion*", Eur J Clin Invest., 2001, 31(5), pages 405-416; Mari et. al., "*Meal and oral glucose tests for assessment of beta-cell function: modeling analysis in normal subjects*", Am J Physiol Endocrinol Metab, 2002, 283(6), E1159-E1166; and Breda et. al., "*Insulin release in impaired glucose tolerance: oral minimal model predicts normal sensitivity to glucose but defective response times*", Diabetes, 2002, 51(1), S227-S233.

More sophisticated models are described by Pedersen et. al., "*Intra-and inter-islet synchronization of metabolically driven insulin secretion*"; Biophys J., 2005, 89(1), pages 107-119; Bertuzzi et. al., "*Insulin granule trafficking in beta-cells: mathematical model of glucose-induced insulin secretion*", Am J Physiol Endocrinol Metab., 2007, 293, E396-E409; Chen et. al., "*Identifying the Targets of the Amplifying Pathway for Insulin Secretion in Pancreatic β-Cells by Kinetic Modeling of Granule Exocytosis*"; Biophysical Journal, 2008, 95(5), pages 2226-2241.

Although any of these kinds of computational models may be used by processing logic 108, they may be either too simplistic or too complex. The minimal models may result in a relatively inaccurate estimation of the predicted insulin level of a patient or user. The sophisticated models may be too complex due to the large number of parameters and equations making them difficult to use or implement using closed-loop control algorithms.

A insulin secretion computational model described by Pedersen et al., "*Cellular modeling: insight into oral minimal models of insulin secretion*", Am J Physiol Endocrinol Metab., 2010, 298, E597-E601, is used herein, by way of example only, by processing logic 108 in controller unit 102. This model will be referred to as the Pedersen model. However, it is to be appreciated that different insulin secretion computational models may be used to provide a predicted patient insulin level based on a measured concentration or level of blood glucose for the patient or user and/or the patient's or user's behaviour such as ingesting a meal or not.

Figure 3:
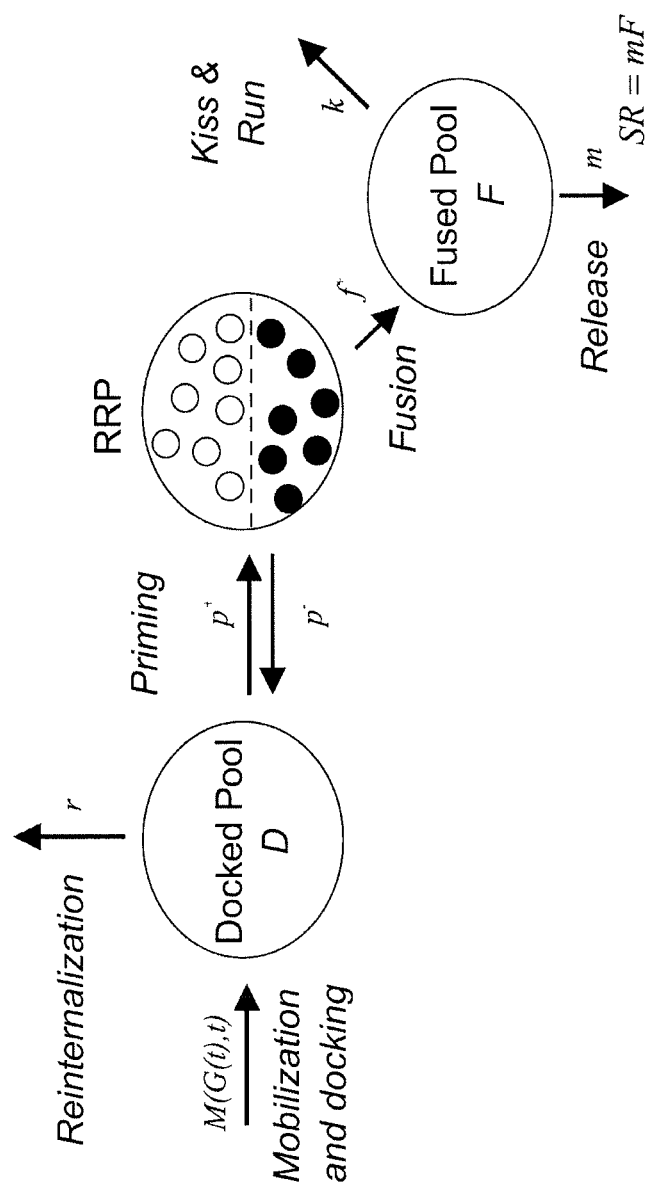
FIG. 3 illustrates schematically a pancreatic beta-cell insulin secretion computational model.

FIG. 3 illustrates the Pedersen model, which is a pancreatic beta-cell computational model and is able to represent most of the experimental data, including the bi-phasic response of insulin secretion, the 'staircase' modulation of insulin secretion, the potentiation effect of glucose and kiss-and-run of insulin secretion granules. Furthermore, its relative simplicity makes it convenient for practical implementation. The Pedersen model includes mobilization of secretory granules from a reserve pool to the cell periphery, where they attach to the plasma membrane (docking). The granules can mature further (priming), thus entering the 'readily releasable pool' (RRP). Calcium influx triggers membrane fusion and subsequent insulin release. The possibility of so-called kiss-and-run exocytosis is included, where the fusion pore reseals before the granule cargo is released. The glucose-dependent increase in the number of cells showing a calcium signal as described in Grodsky, "*A threshold distribution hypothesis for packet storage of insulin and its mathematical modelling*", J Clin Invest, vol. 1972, 51(8), pages 2047-2059, is included by distinguishing between readily releasable granules in silent and active cells. This means the RRP is heterogeneous in the sense that only granules residing in cells with a threshold for calcium activity below the ambient glucose concentration are allowed to fuse.

The readily releasable pool (RRP) has been divided into readily releasable granules located in silent cells with no calcium influx, exocytosis, or release (circles) and readily releasable granules located in triggered cells (dots). Mobilisation is assumed to depend on glucose but with a delay τ, as described in Grodsky et. al, is given as $$\frac{dM(t)}{dt} = \frac{M_\infty(G)}{\tau}. \tag{1}$$

The docked pool develops according to the mass-balance equation $$\frac{dM(t)}{dt} = M(G, t) - rD(t) - p^+ D(t) + p^- \int_0^\infty h(g, t)\,dg. \tag{2}$$

where M is the mobilization flux and r is the rate of reinternalization. The last two terms describe priming and depriming of granules, respectively. The RRP is described by a time-varying density function h(g,t), indicating the amount of insulin in the RRP in β-cells with a threshold between g and g+dg. Granules are primed with rate $p^+$ and are assumed to lose the capacity of rapid exocytosis with rate $p^-$. Moreover, if the granule is in a triggered β-cell, i.e., a cell with a threshold below the glucose concentration, it will fuse with rate $f^+$. This leads to the equation $$\frac{\partial h(g, t)}{\partial t} = p^+ D(t) - p^- h(g, t) - f^+ h(g, t)\theta(G - g). \tag{3}$$

Here, θ(G−g) is the Heaviside unit step function, which is 1 for G>g and zero otherwise, indicating that fusion occurs only when the threshold is reached. The priming flux $p^+D$ distributes among cells according to the fraction of cells with threshold g described by the time-independent function φ(g). Priming is assumed to occur with the same rate in all cells, but the fraction of cells is taken into account with the corresponding threshold.

The secretion rate or predicted patient insulin output level can be expressed as $$SR(t) = mF(t) + SR_b(t), \tag{4}$$

where $SR_b$ is the basal insulin secretion, m is the rate constant of release, and F is the size of the fused pool, which follows, $$\frac{dF(t)}{dt} = f^+ h(g, t)dg - F(t) + mF(t), \tag{5}$$

where $f^+$ is the rate constant of fusion and k is the kiss-and-run rate. The integral represents the amount of insulin in the RRP in cells with a threshold below G.

Embodiments of the invention use the Pedersen computational model, by way of example only, with the model parameter values taken from Pedersen et. al 2010, which are shown in Table 1. It is to be appreciated that these parameters are by way of example only and that any suitable computational model may be used along with any suitable set of parameters.

TABLE 1

Model parameters from Pedersen et. al. 2010

| Parameter | Value |
|---|---|
| m (min) | 0.62 |
| $f^+$ (min) | 6.2 |
| k (min) | 0.47 |
| $p^+$ (min) | 0.03 |
| $p^-$ (min) | 0.1 |
| r (min) | 0.008 |
| $M_0$ (g/min) | 1.4 |
| c (g/min) | 20 |
| $K_{mM}$ (mM) | 10 |
| nM | 4 |
| Kφ (mM) | 7.22 |
| n | 3 |
| τ (min) | 15 |
| $SR_b$ (g/min) | 0.58 |

An example of using the Pedersen model in a bio-inspired controller using an intravenous (i.v.)-type measurement for controlling the output insulin level of an insulin pump is now described. The controller is referred to as an i.v.-i.v. controller. The Pedersen model is used, by way of example only, for the glucose-stimulated pancreatic insulin secretion model to control a 10 member adult population described in the commercial version of the T1DM simulator of Kovatchev et. al. 2009. An i.v. route is used for glucose sensing and insulin delivery to a patient or user. Due to inter-patient insulin sensitivity and variability, a tuneable gain factor K was added to the dynamic term of equation 4, which provides the secretion rate or the predicted patient insulin output. Furthermore, as the Pedersen model does not include the inhibition of the basal insulin secretion at low glucose concentrations, a variable gain Kb was added multiplying this term. The control signal is generated from the patient insulin deficiency level, which can be described as:

$$SR(t) = K \cdot m \cdot F(t) + K_b SR_b(t).$$

where $K_b$ is a variable gain that is calculated as $$K_b = \min\left(1, \frac{(G - G_{lim})}{(G_{sp} - G_{lim})}\right), \tag{6}$$

where $G_{sp}$ is the glucose set-point (e.g., 90 mg/dL) and $G_{lim}$ is the threshold to start the inhibition (e.g., 80 mg/dL).

To illustrate the performance of the i.v.-i.v. controller, an example simulation using the i.v.-i.v. controller was performed for a meal containing 75 grams of carbohydrates for 10 subjects (e.g. patients or users). The basal insulin infusion rate was manually adjusted for each subject and the gain factor K was individually tuned to keep the 10 subjects inside the blood glucose concentration range [70, 200] mg/dL. It was observed that only one subject, (subject #9), required dividing the parameter c of the Pedersen model by 2 in order to reduce the magnitude of the second phase and avoid hypoglycemia.

Figure 4:
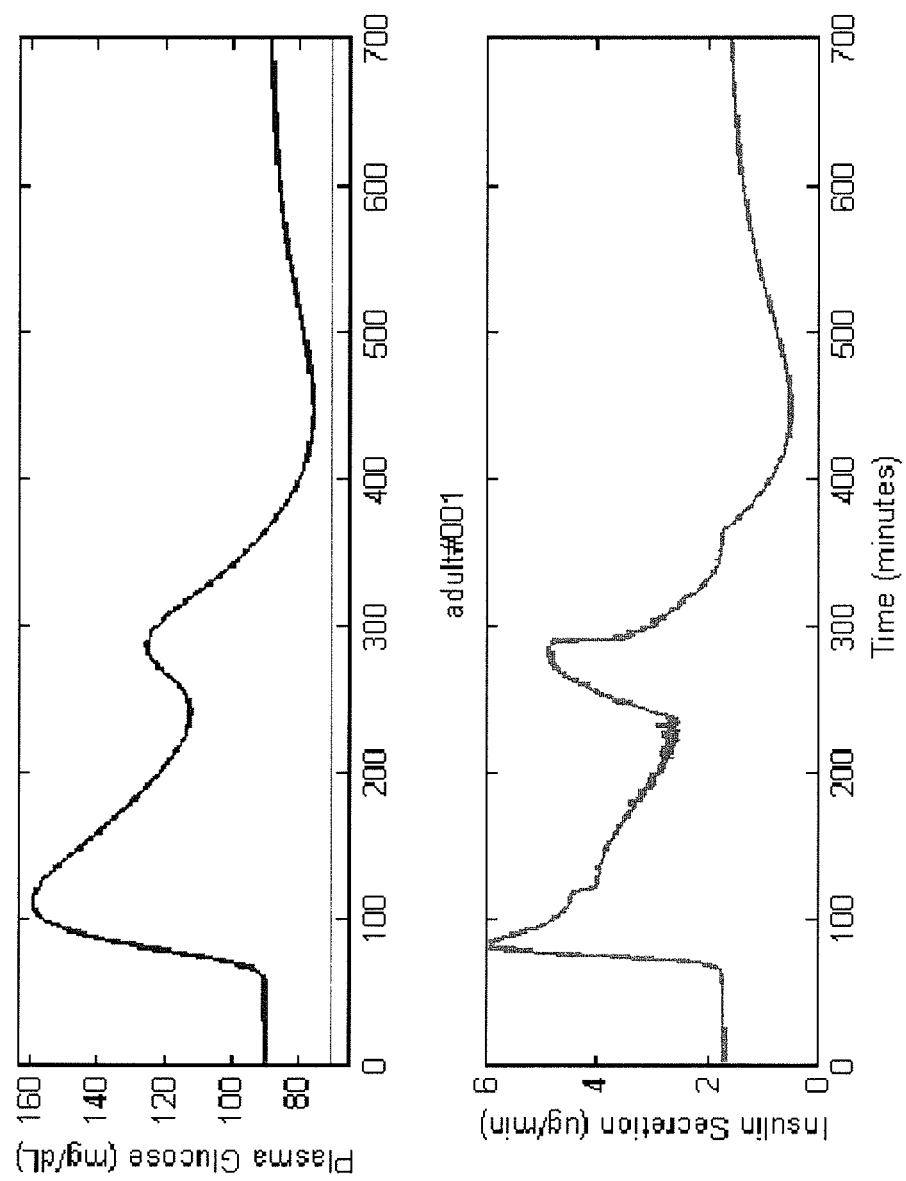
FIG. 4 illustrates example graphs of biphasic insulin secretion controlled by an apparatus according to the invention.

FIG. 4 shows two graphs illustrating the results of the i.v.-i.v. controller corresponding to subject #1. The y-axis of the upper graph represents plasma glucose (mg/dL) and the y-axis of the lower graph represents insulin secretion (ug/min), where the x-axis on both graphs represents time in minutes. The upper graph, illustrates the expected Plasma glucose concentration corresponding to a meal containing 75 grams of carbohydrates. The lower graph illustrates Insulin delivery of the i.v.-i.v. controller. Although the i.v.-i.v. control is optimal from a control perspective, it should be used under supervision, for example, in-hospital applications such as critical care. However, the i.v.-i.v. controller is not suitable for an ambulatory or mobile artificial pancreas due to time delays and noise introduced.

Current technologies for continuous glucose sensing and insulin delivery primarily use the subcutaneous route, the main problem of which is the time delays introduced on glucose sensing (up to 15 minutes) and insulin action (15-20 minutes). The variability of these delays can be high and the accuracy of the current s.c. continuous glucose sensors is far from being optimal with mean absolute differences of up to 20%, especially in hypoglycaemia, which is the critical state to avoid.

Figure 5A:
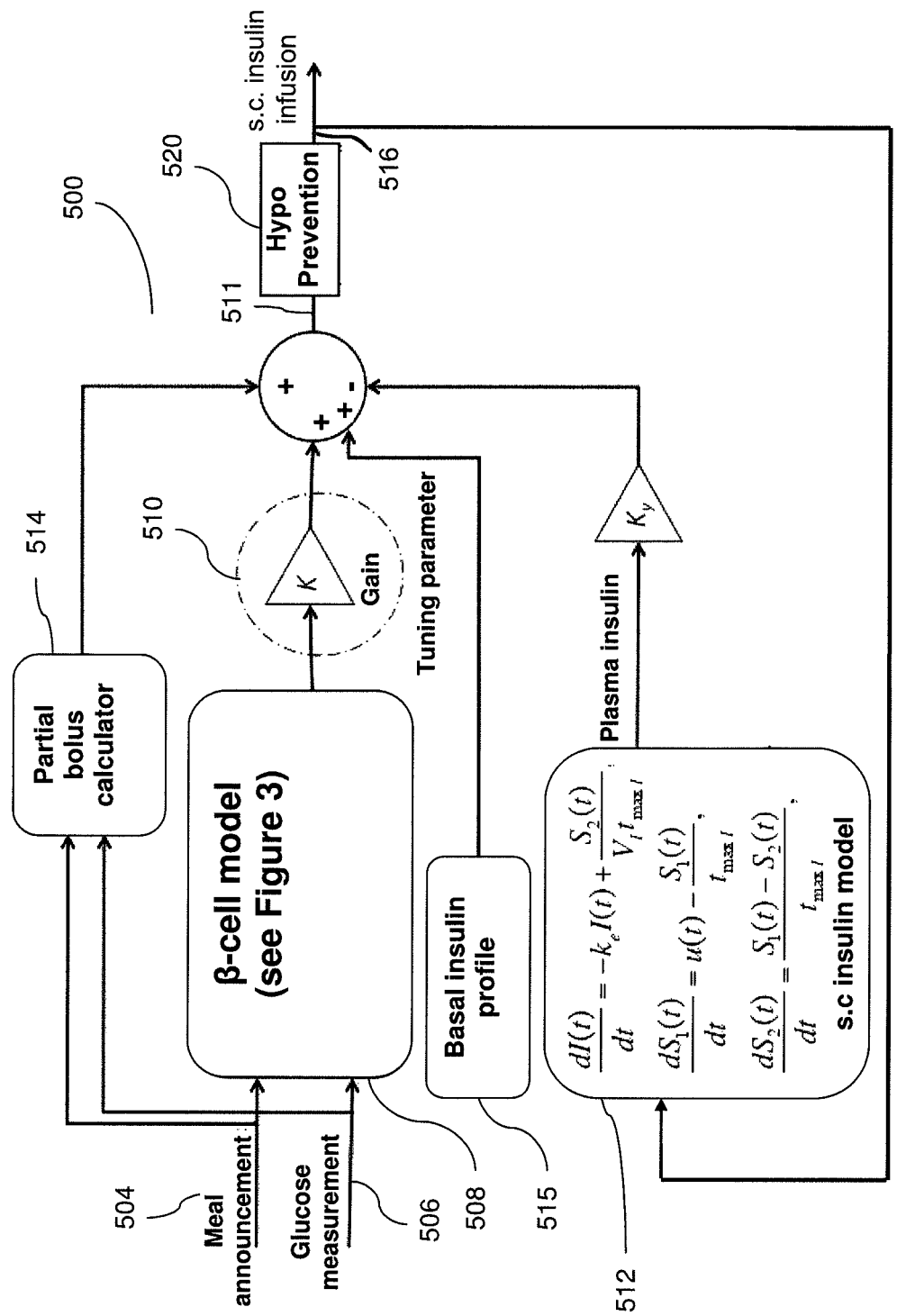
FIG. 5a illustrates another apparatus according to the invention for controlling an insulin pump.
Figure 5B:
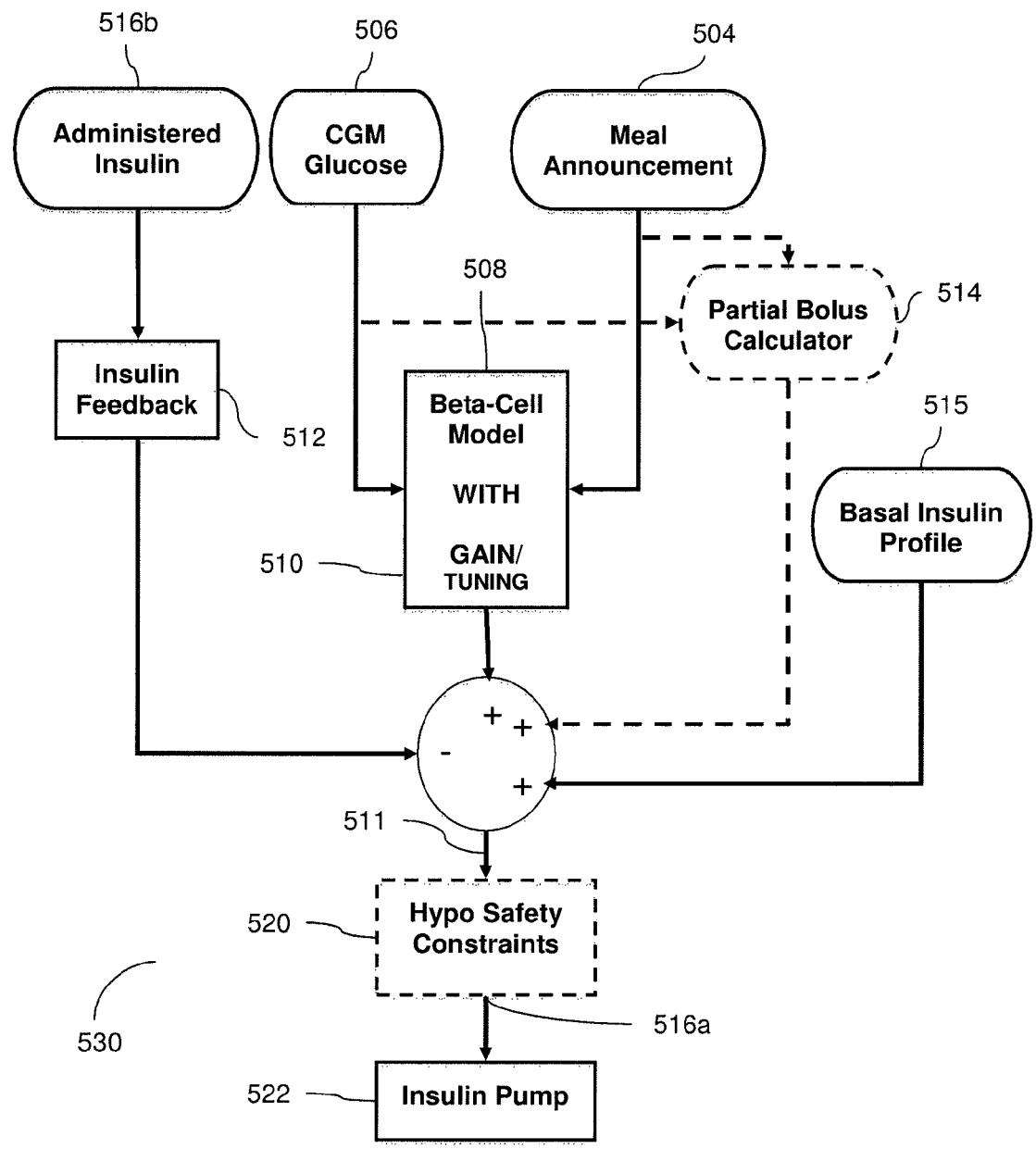
FIG. 5b illustrates another apparatus according to the invention for controlling an insulin pump.

FIG. 5b illustrates a schematic diagram of a controller unit 500 according to another embodiment of the invention for use in controlling an insulin pump (not shown). The controller unit 500 uses glucose sensing and insulin delivery via the subcutaneous (s.c.) route. The controller unit 500 includes a glucose measurement input 506 for receiving data representative of the concentration or level of blood glucose of a user or a patient. The controller unit 500 is an s.c.-s.c. closed loop glucose controller and includes beta-cell processing logic 508 based, by way of example, on the Pedersen model of glucose-stimulated pancreatic insulin secretion. The beta-cell processing logic 508 outputs a predicted patient insulin level based on data received from user input 504 and measurement input 506. Gain logic 510 is applied to the predicted patient insulin level to determine a patient insulin deficiency level 511 based on one or more gain factors K i.e. a gain factored predicted patient insulin level. Included in the controller unit 500 is s.c. insulin feedback logic 512 and partial bolus calculation logic 514, which provide an insulin feedback level and a bolus insulin level, respectively. The patient insulin deficiency level 511 is calculated based on the gain factored predicted insulin level, the bolus insulin level, and insulin feedback level for generating control signal 516. In addition, a basal insulin profile logic 515 may be incorporated, if needed, for providing a basal insulin level for use in generating the control signal 516. As a safety measure, hypo prevention logic 520, may be included to minimise or prevent hypoglycemia. In this example, the patient insulin deficiency level 511 is calculated by summation of the gain factored predicted patient output level, the bolus insulin level, the insulin feedback level, and the basal insulin level, which are used to generate control signal 516.

The main problem associated to the delays in the glucose sensing and insulin delivery is excess insulin overdosing and the consequent risk of hypoglycemia, in particular post-prandially or after a meal. One solution to deal with this problem is to incorporate an insulin feedback level, which was described in G. M. Steil et. al., "*Feasibility of automating insulin delivery for the treatment of type 1 diabetes*", Diabetes, 2006, 55, pages 3344-3350. This term constrains the insulin delivery based on an estimate of the plasma insulin concentration (insulin-on-board). The patient deficiency output level 511 that is used to generate the control signal 516 at the output of the controller unit 500 can be expressed as $$U(t) = SR(t) - K_y I(t) \quad (7)$$

where I(t) is an estimate of the plasma insulin concentration (relative to the basal conditions) and $K_y$ is a tuning gain. The s.c. insulin feedback logic 512 is based on modelling the insulin absorption pharmacodynamics and estimates the plasma insulin concentration, by way of example, an insulin absorption model described in Hovorka et. al., "*Nonlinear model predictive control of glucose concentration in subjects with type 1 diabetes*", Physiol. Mea., 2004, 25, pages 905-20 can be used. The equations of this model are $$\frac{dI(t)}{dt} = -k_e I(t) + \frac{S_2(t)}{V_I t_{max\, I}},$$

$$\frac{dS_1(t)}{dt} = u(t) - \frac{S_1(t)}{t_{max\, I}},$$

$$\frac{dS_2(t)}{dt} = \frac{S_1(t) - S_2(t)}{t_{max\, I}},$$

where, $k_e$ is the first order decay rate for insulin in plasma, u(t) subcutaneous insulin infusion rate, $V_I$ is the distribution volume of plasma insulin, $t_{maxi}$ is the time-to-maximum insulin absorption, $S_1(t)$ and $S_2(t)$ are a two-compartment chain representing absorption of subcutaneously administered short-acting (e.g. Lispro) insulin. The parameters of this feedback model are fixed to mean population values proposed by the same author.

Controlling glucose levels in T1DM subjects (patients or users) is difficult due to the glucose excursion after the ingestion of a meal. Due to the previously mentioned delays, the controller unit 500 needs to be more aggressive at the beginning of the glucose excursion in order to minimize the post-prandial hyperglycemia. However, during late post-prandial or fasting conditions, the controller needs to be less aggressive to minimise the risk of insulin stacking. The predicted patient insulin level output from beta-cell processing logic 508 is adjusted by gain logic 510 using gain factor K according to $$SR(t) = K \cdot m \cdot F(t)$$

The gain K may be set at different times, so instead of using a single gain factor (K), several gain factors may be used depending on the varying conditions the insulin pump will operate over. This produces a gain factored predicted patient insulin output level. In this embodiment of the gain logic 510, three gain factors (Kp, Kh and Kf) are used, by way of example only. It is to be appreciated that more gain factors, or sets of gain factors may be used to further optimise the control of the insulin pump.

The first gain factor, (Kp), is used for a certain period of time (Tp) after the ingestion of a meal. The second gain factor, (Kh), is used at all other times when the glucose concentration is above a predetermined glucose threshold (eg. 180 mg/dL). The predetermined glucose threshold is calculated from the historical data of the patient and their insulin requirements. The third gain factor, (Kf), is used otherwise. Note, snacks (i.e., <20 grams of carbohydrates) are not considered as proper meals and so either the second or third gains can be used in this situation. However, it is to be appreciated that more gain factors could be determined that better fit the conditions of a given situation.

The gain logic 510 can set gain factor K to Kf, Kp, or Kh according to:

if $t > T_{meal}$ and $t < T_{meal} + T_p K = K_P$ else if $G(t) > 180\ K = K_h$ else $K = K_f$ The basal insulin attenuation gain (Kb) as described in Equation 5 may be removed from the patient deficiency output level 511 for generating control signal 516 when it is considered that the glucose sensor error is too large.

In addition to the above features, the controller unit 500 may also be configured to include partial bolus calculator 514 that calculates a pre-meal partial bolus due to delays introduced by the s.c. measurement and delivery route. A partial pre-meal bolus may be used to deliver part of the required insulin before a meal is ingested in order to match the insulin action peak with the carbohydrate absorption peak, and minimise the post-prandial excursion. In order to calculate this partial bolus, extra information about the amount of carbohydrates (CHO) of the ingested meal is needed. The controller unit 500 may receive the extra information required by partial bolus calculator 514 from user input 504 and/or measurement input 506. Such information may include data representative of a user notifying the controller of an imminent meal and/or an estimate of the amount of carbohydrates that may be ingested. Using the insulin-to-carbohydrate ratio (ICR) and the correction factor (CF) for the user or the patient, a patient specific or corresponding partial bolus (PB) can be calculated by the partial bolus calculator 514 as follows:

$$PB(t) = 0.5 \frac{CHO(t)}{IRC} + \frac{G(t) - G_{sp}}{CF},$$

where G is the glucose concentration and $G_{sp}$ is the glucose set-point. The bolus can be delivered prior to a meal, for example 10 minutes before of the ingestion of the meal. The partial bolus insulin level is only part of the required insulin for the user or patient, it is not all of the required insulin.

Given the outputs of the gain logic 510, s.c. insulin feedback logic 512, and partial bolus calculator 514, the controller unit 500 can be configured to calculate a patient deficiency level 511 for generating a control signal 516 based on the following equation:

$$U(t) = SR(t) - K_y I(t) + PB(t).$$

where U(t) is the patient deficiency output level 511 for generating control signal 516, SR(t) is the gain factored predicted patient insulin output level adjusted by gain factor K, $K_y I(t)$ is the estimated insulin feedback level of the plasma insulin concentration, and PB(t) the calculated pre-meal partial bolus level. The basal insulin level may or may not be included depending on the patient's insulin requirements.

The controller unit 500 may also include hypoglycaemia (hypo) prevention logic 520, which is a safety mechanism that minimises and/or prevents hypoglycaemia. This minimises the possible risk of over-delivery of insulin due to the algorithm calculations. The hypo prevention logic can be used in conjunction with the processing logic that calculates the patient deficiency output level 511 and generated control signal 516 for controlling the insulin pump. This mechanism limits the amount of insulin that the insulin pump is allowed to infuse during both, fasting conditions and prandial conditions. These safety constraints are based on measured parameters such as body weight, correction factor, insulin-to-carbohydrate ratio and total daily insulin requirements.

The safety constraints include fasting constraints, which includes a maximal basal insulin level and basal insulin-on-board level. The maximal basal insulin level limits the delivered insulin during a certain amount of time based on the total daily insulin requirements. The basal insulin-on-board level limits the basal insulin delivery when the insulin-on-board estimation (i.e. active insulin in the body of the patient) reaches a predefined on-board threshold. The safety constraints also include postpandrial constraints, which in clued maximal bolus and postprandial insulin-on-board levels. The maximal bolus level limits the insulin bolus associated to a meal based on the correction factor and the insulin-to-carbohydrate ratio of the patient. The postprandial insulin-on-board level limits the postprandial insulin delivery when the insulin-on-board estimation reaches a predefined limit. Hypoglycemia can then be predicted based on a validated glucose forecasting algorithm, the insulin pump shuts off when a hypoglycemia is predicted in an N minute time horizon (e.g. N=20, 30, or 40 minutes).

The hypo prevention logic 520 is used in conjunction with the controller unit 500 to suppress, or reduce, insulin delivery when low glucose values are predicted. An example of performing this function is described in E. Dassau et. al., "*Real-time hypoglycaemia prediction suite using continuous glucose monitoring: a safety net for the artificial pancreas*", Diabetes Care, 2010, 33, pages 1249-1254. The hypo prevention logic 520 is configured to forecast the glucose concentration (e.g., 20 minutes ahead) and to stop or reduce the insulin delivery of the insulin pump controlled by patient insulin deficiency level (U(t)) 511 and control signal 516 if the glucose levels fall below a predefined threshold. The predefined threshold may be user or patient specific. As an example, the hypo prevention logic 520 may adjust the patient insulin deficiency level (U(t)) 511 and hence the control signal 516 based on the following logic:

if $G(t) + S \cdot H < 70 \Rightarrow U(t) = 0$, else if $G(t) + S \cdot H < 90 \Rightarrow U(t) = 0.5 U(t)$, (8)

where G(t) is the current glucose value, H is the forecasting horizon or window, and S is the slope of a linear regression calculated using the previous n samples. It is to be appreciated that the predefined glucose safety thresholds or limits 70 and 90 may be adjusted depending on the patient's or user's insulin requirement.

The controller unit 500 can be adjusted to provide optimal control for the delivery of insulin for each user or patient. The controller unit 500 can be individually tuned. To do this, the patient or user can be studied or examined to determine data representative of their basal insulin requirements to optimise glycemia. The controller unit 500 is able to tackle possible mismatches, as well as possible perturbations such as exercise. As an example, the controller unit 500 parameters to be tuned are: the first, second and third gain factors Kp, Kf, and Kh, the period Tp for which the post-prandial gain (Kp) is valid, insulin feedback gain (Ky), the number of samples used for the linear regression (n) and the forecasting horizon (H), and the glucose set-point (Gsp). In addition, the model parameters of the insulin secretion computational model may need to be tuned. In this case the Pederson model (a pancreatic beta-cell model) is used as the insulin secretion computational model.

These parameters can be tuned based on the historical data of the patient or user. From tests, it has been seen that the parameters have low inter-patient or subject variability and can generally be fixed without significantly affecting the performance of the controller. The only parameter that needs to be individually tuned to the patient or user is the gain factors Kp, Kh, and Kf. This poses a 3-dimensional optimisation problem, which can be computationally expensive when optimising over large data sets. However, the gain factors Kh and Kf may be set to be proportional to Kp. By way of example only, based on the T1DM simulated population, Table 2 shows the parameter values (not including model parameters) that were determined and used in simulations by the controller unit 500.

TABLE 2 tuning parameters used in simulations of the controller unit 500

| Parameter | Value |
| --- | --- |
| $K_y$ | 15 |
| $T_p$ | 1 h |
| $K_h$ | $0.5 * K_p$ |
| $K_f$ | $0.2 * K_p$ |
| n | 30 min |
| H | 20 min |
| $G_{sp}$ | 100 mg/dL |

Although it may be possible to tune parameter Kp during an in-vivo study, it is not recommended for evident safety reasons. This means an off-line auto-tuning methodology should be implemented for this purpose. For example, the historical data (also called ambulatory data) for a patient can be collected during one or more visits to a skilled engineer, nurse or doctor. For example, the patient may have had a first and second visit, from the results of these visits. The historical data can include blood glucose measurements, for example continuous glucose monitor measurements (CGM), capillary blood glucose measurements (1 pre-prandial and 1 post-prandial at 90 minutes for example), insulin pump data and carbohydrate ingestion (estimated from food diaries).

Historical data is selected based on a scenario where a good glycaemic control was achieved during these visits. The selected historical data is downloaded and compiled into a format suitable for analysis. Using the selected historical data, the controller 500 is tuned using optimisation analysis, which can be performed using software run on a personal computer. The optimisation analysis algorithm uses the selected historical data (for example the CGM data, total insulin delivered and carbohydrates ingestion) to calculate the controller parameters such as the gain factors and other tuning parameters for the insulin secretion model used by the controller 500. This ensures the controller 500 will deliver the same amount of insulin as during the selected scenario.

Once the controller parameters have been obtained using the optimisation analysis they may be input into the controller 500. For example, user input 504 may include a connector for receiving the controller parameters from the computer (e.g. via USB or wirelessly), or user input may include a connection for receiving the controller parameters via a removable or portable memory such as a Micro SD Card™ controller. Alternatively of in addition to these inputs, user input 504 may include a connection to a keypad or keyboard in which the controller parameters are entered manually. In any event, user input receives the controller parameters, which include the gain factor(s) that were calculated during the optimisation algorithm. In addition the insulin secretion computational model and/or its parameters may be uploaded to the controller unit 500.

In an example, the methodology uses open-loop historical data from the patient, user or studied subject (i.e. meal information, continuous glucose monitor data, and insulin pump data) that corresponds to a "good" or successful glucose control scenario and similar conditions with respect to the planned closed-loop test (i.e., similar meals, time of the day, exercise, etc). This auto-tuning methodology includes an optimization algorithm that adjusts the gain factor Kp, such that, for the given glucose profile, the controller delivers the same amount of insulin that was administered during the open-loop scenario.

As a simple test example of tuning the controller unit 500, historical open-loop data was generated from the metabolic test functionality of the T1DM simulator and used to tune the controller unit 500. The historical data could also be based on real-world data from studies or examinations of a patient or user. The T1DM simulator generated historical data based on a 24 hour scenario with a single meal of 60 g of carbohydrates ingested 3 hours after the beginning of the scenario. The basal insulin rate (SRb) was adjusted to achieve a basal glucose concentration close to 100 mg/dL. Then, the insulin-to-carbohydrate ratio was adjusted in order to achieve a post-prandial inverse response (i.e. undershoot) close to 80 mg/dL. The resulting glucose profile was then used to tune controller unit 500. The fmincon function from the Matlab™ Optimization Toolbox (2010b, The Matworks, Natick, Mass.) was used to find the gain factor Kp that minimised the following cost function:

$$J = \int_0^T U(t)\,dt - \left(\int_0^T SR_b(t)\,dt + \frac{CHO}{ICR}\right),$$

where T is the duration of the scenario (i.e. 24 hours), CHO is the amount of ingested carbohydrates (i.e. 60 g) and ICR is the calculated insulin-to-carbohydrate ratio. The gain factor Kp was constrained to be within the range [0, 3). However, it is to be appreciated that different insulin computational models may require different ranges and constraints.

FIG. 5b illustrates a schematic diagram of another example of a controller unit 530 for use in calculating a control signal 516a for controlling an insulin pump 112. Controller unit 530 uses similar components as controller unit 500 of FIG. 5a and hence the reference numerals have been reused for simplicity, where each component has been described with reference to FIG. 5a.

Controller unit 530 uses continuous glucose monitoring or sensing from a glucose measurement input 506, which can use a sensor from, but not limited to, the group of a subcutaneous blood glucose sensor, intravenous blood glucose sensor, and a non-invasive blood glucose sensor. Glucose measurement input 506 receives data representative of the concentration or level of blood glucose of a user or a patient. The controller unit 500 is a closed loop glucose controller and includes beta-cell processing logic 508 (a pancreatic beta-cell computational model) based, by way of example, on the Pedersen model of glucose-stimulated pancreatic insulin secretion. The beta-cell processing logic 508 outputs a predicted patient insulin level based on data received from user input 504 (such as meal announcements and/or carbohydrate amounts) and measurement input 506. Gain logic 510 uses the predicted patient insulin level to determine a gain factored predicted patient insulin level based on one or more gain factors K for calculating the patient insulin deficiency level 511. Included in the controller unit 500 is insulin feedback logic 512 to provide the insulin feedback level, which is based on insulin administered to the patient, which can be measured from the output of insulin pump 522 or derived from control signal 516a. Optionally partial bolus calculation logic 514 shown as dashed indicating it is not necessary for some controllers, can provide a bolus insulin level when implemented, but this is not necessary as seen below. The patient insulin deficiency level 511 is calculated by summation of the gain factor predicted insulin output level, the optional bolus insulin level, and insulin feedback level, which is then used for generating control signal 516a. In addition, a basal insulin profile logic 515 may be incorporated, if needed, for providing a basal insulin level in calculating patient insulin deficiency level 511 for use in generating the control signal 516a.

As a safety measure, hypo prevention logic 520, may optionally be included to minimise or prevent hypoglycaemia, which adjusts or limits the patient insulin deficiency level 511 and thus adjusts or limits the control signal 516*a*. The control signal 516*a* is then used to control the output insulin level of insulin pump 522.

If the controller 530 is used without a pre-meal bolus, then it will only require the meal to be announced by the user, which can be done by just pressing a button included in user input 504. The pre-meal bolus modality, i.e. when the partial bolus calculator 514 is implemented, requires additional information about the meal (i.e. amount of carbohydrates), which can be easily introduced through a graphical user interface. The selection between these two strategies could depend on the type of user or patient to be treated. For a children population, it would be more convenient to just press a button to tell the controller unit 530 about a meal or snack. For an adolescent/adult population, the patient or user can be asked for more information about the meal or snack so that the partial bolus calculator could be implemented in controller unit 530. The controller units 500 and 530 can be embedded in a portable artificial pancreas or insulin pump, which includes the electronic instrumentation to interface with a glucose sensor e.g. a continuous glucose sensor.

Figure 6:
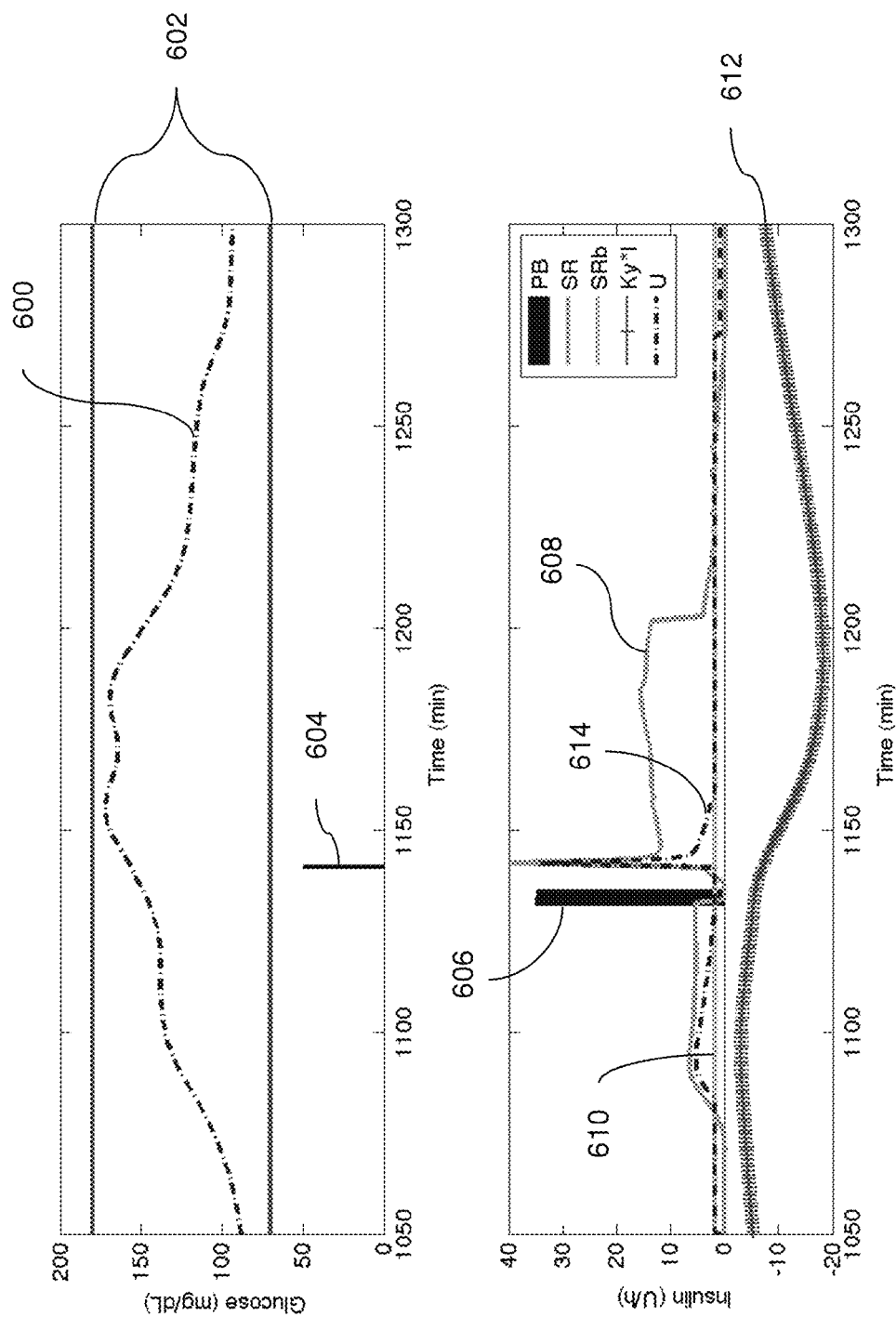

FIG. 6 illustrates a graph showing an example of insulin delivery by an insulin pump controlled by controller unit 500 for a portion of the above-mentioned scenario. The y-axis of the upper graph represents glucose (mg/dL) and the y-axis of the lower graph represents insulin (ug/min), where the x-axis on both graphs represents time in minutes. The upper graph illustrates subcutaneous glucose measurements 600 (dashed blue line); hyper- and hypoglycemia thresholds 602 (red horizontal lines) and meals 604 (bars). The lower graph illustrates pre-meal partial bolus 606 (blue bar), B-cell model insulin secretion 608 (solid green line), basal insulin 610 (solid cyan line), insulin feedback 612 (starred red line) and delivered insulin 614 (blue dashed line).

In addition to the above-mentioned processes, there is provided a method of controlling blood glucose levels within a patient, which includes calculating a gain factor for the patient based upon historical data in relation to the patient, measuring a blood glucose level in the patient, applying the measured blood glucose level to a insulin secretion computational model to predict an insulin output level, calculating a patient insulin deficiency level based on said gain factor and the predicted insulin output level, and using the patient insulin deficiency level as a control input for an insulin pump configured to pump insulin into the patient at the subcutaneous level. This method can be used for treating diabetics (for example people with type 1 or type 2 diabetes) in-situ or when mobile using an ambulatory or portable insulin pump.

The controller units described above and with reference to FIGS. 2*a*, 2*b*, 5*a*, and 5*b* may include a processor or processing logic or field programmable gate arrays, including memory or logic gates for storing instructions or a computer program, comprising code which, when executed in the processor or processing logic or logic gates, causes the controller unit to perform the method steps as outlined herein. Such computer programs as described herein can be incorporated within one or more computer program products, each comprising a computer readable medium and one or more of the computer programs, where one or more of the computer programs are stored on the computer readable medium. The controller units as described above and with reference to FIGS. 2*a*, 2*b*, 5*a*, and 5*b*, e.g. controller units 102, 500, or 530, may also be implemented as one or more integrated circuits such as, but not limited to, a semiconductor device or chip, a complementary metal-oxide-semiconductor (CMOS) device or chip, a field programmable gate array (FPGA), application-specific integrated circuits (ASIC) or any other appropriate integrated circuit or device.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated into the invention, whether alone or in any appropriate combination with any other feature disclosed or illustrated herein.

The invention claimed is:

1. An apparatus for controlling an insulin pump, the apparatus comprising:
   a user input for receiving a first gain factor, the first gain factor having been calculated based on historical data in relation to a patient;
   a measurement input for receiving data representative of a measured blood glucose level for the patient; and
   processing logic configured to:
   apply the measured blood glucose level to an insulin secretion computational model to predict an insulin output level;
   apply the first gain factor to the predicted insulin output level to determine a patient insulin deficiency level; and
   calculate a control signal for controlling the insulin output level of the insulin pump based on the patient insulin deficiency level;
   wherein the processing logic is configured to apply the first gain factor to the predicted insulin output level for a first period of time after ingestion of a meal by the patient;
   wherein the first gain factor is arranged to be tuned to the patient by minimizing a predicted insulin output level cost function based on historical data of the patient; and
   wherein the user input receives a second and third gain factors, the second and third gain factors having been calculated based on the historical data in relation to the patient, and the processing logic being configured to:
   apply the second gain factor to the predicted insulin output level when the blood glucose level for the patient is equal to or above a predetermined glucose threshold; and
   apply the third gain factor to the predicted insulin output level when the first period of time expires and when the blood glucose level for the patient is below the predetermined glucose threshold.

2. An apparatus according to claim 1, wherein the user input is configured to receive an indication of a meal to be ingested and the processing logic applies the indication to the insulin secretion computational model to predict the insulin output level for the patient.

3. An apparatus according to claim 2, wherein the processing logic is further configured to:
   calculate a pre-meal insulin level based on the measured blood glucose level and the indication of a meal to be ingested; and
   calculate the patient deficiency level and the control signal using the pre-meal insulin level.

4. An apparatus according to claim 3, wherein the indication of a meal to be ingested further includes data representative of the amount of carbohydrates of the meal to be ingested.

5. An apparatus according to claim 1, wherein the processing logic further configured to:

calculate a feedback insulin level based on estimating a plasma insulin concentration from the insulin output level of the insulin pump; and calculate the patient deficiency level and the control signal using the feedback insulin level.

6. An apparatus according to claim 1, wherein the insulin secretion computational model is a pancreatic beta-cell computational model.

7. An apparatus according to claim 1, provided as an integrated circuit.

8. An apparatus according to claim 7, wherein the integrated circuit is a complementary metal-oxide-semiconductor (CMOS) device or chip.

9. An apparatus according to claim 1, wherein the measured blood glucose level is measured from a blood glucose sensor from the group of a subcutaneous blood glucose sensor, intravenous blood glucose sensor, and a non-invasive blood glucose sensor.

10. The apparatus according to claim 1, wherein the historical data comprises an amount of ingested carbohydrate and an insulin-to-carbohydrate ratio of the patent.

11. An insulin system for use by a patient comprising an insulin pump for the patient, a blood glucose sensor for the patient, and an apparatus according to claim 1 for use in controlling the insulin output level of the insulin pump, the apparatus connected to the insulin pump and the blood glucose sensor.

12. An insulin system according to claim 11, wherein the blood glucose sensor is a sensor from the group of a subcutaneous blood glucose sensor, intravenous blood glucose sensor, and a non-invasive blood glucose sensor.

13. An insulin pump comprising an apparatus according to claim 1 for controlling the output insulin level of the insulin pump.

14. A method for controlling an insulin pump, the method comprising:
    receiving a first gain factor, the first gain factor having been calculated based on historical data in relation to a patient;
    receiving data representative of a measured blood glucose level for the patient;
    applying the measured blood glucose level to an insulin secretion computational model to predict an insulin output level;
    applying the first gain factor to the predicted insulin output level to determine a patient insulin deficiency level; and
    calculating a control signal for controlling the insulin output level of the insulin pump based on the patient insulin deficiency level;
    wherein the first gain factor is arranged to be tuned to the patient by minimizing a predicted insulin output level cost function based on historical data of the patient.

15. A method according to claim 14, wherein the first gain factor is applied to the predicted insulin output level for a first period of time after ingestion of a meal by the patient.

16. A method according to claim 15, further comprising receiving second and third gain factors, the second and third gain factors having been calculated based on the historical data in relation to the patient, and the method further comprising:
    applying the second gain factor to the predicted insulin output level; and
    applying the third gain factor to the predicted insulin output level when the first period of time expires and when the blood glucose level for the patient is below the predetermined glucose threshold.

17. A method according to claim 14, further comprising receiving an indication of a meal to be ingested, wherein the step of applying the measured blood glucose level further includes applying the indication to the insulin secretion computational model to predict the insulin output level for the patient.

18. A method according to claim 17, further comprising:
    calculating a pre-meal insulin level based on the measured blood glucose level and the indication of a meal to be ingested; and
    calculating the patient deficiency level and the control signal using the pre-meal insulin level.

19. A method according to claim 18, wherein the indication of a meal to be ingested further includes data representative of the amount of carbohydrates of the meal to be ingested.

20. A method according to claim 14, further comprising:
    calculating a feedback insulin level based on estimating a plasma insulin concentration from the insulin output level of the insulin pump; and
    calculating the patient deficiency level and the control signal using the feedback insulin level.

21. A method according to claim 14, wherein the insulin secretion computational model is a pancreatic beta-cell computational model.

22. A method according to claim 14, wherein the measured blood glucose level is measured from a blood glucose sensor from the group of a subcutaneous blood glucose sensor, intravenous blood glucose sensor, and a non-invasive blood glucose sensor.

23. A method of controlling blood glucose levels within a patient, the method comprising:
    calculating a gain factor for the patient based upon historical data in relation to the patient;
    measuring a blood glucose level in the patient;
    applying the measured blood glucose level to an insulin secretion computational model to predict an insulin output level;
    calculating a patient insulin deficiency level based on said gain factor and the predicted insulin output level; and
    using the patient insulin deficiency level as a control input for an insulin pump configured to pump insulin into the patient;
    wherein the gain factor is arranged to be tuned to the patient by minimizing a predicted insulin output level cost function based on historical data of the patient.

24. A method according to claim 23, wherein the patient is a diabetic patient.

25. A method according to claim 23, wherein the insulin secretion computational model is a pancreatic beta-cell computational model.

26. A method according to claim 23, wherein the measured blood glucose level is measured from a blood glucose sensor from the group of a subcutaneous blood glucose sensor, intravenous blood glucose sensor, and a noninvasive blood glucose sensor.

27. A method of determining one or more gain factors for use in controlling an apparatus according to claim 1, comprising calculating one or more gain factors based upon historical data in relation to a patient and entering the one or more gain factors via the user input of the apparatus.

28. A method according to claim 27, further calculating a first gain factor for a first period of time after ingestion of a meal by the patient.

29. A method according to claim 28, further comprising:
    calculating a second gain factor for when the blood glucose level for the patient is equal to or above a predetermined glucose threshold; and calculating a third gain factor for when the first period of time expires and when the blood glucose level for the patient is below the predetermined glucose threshold.

30. A method according to claim 29, wherein the second and third gain factors are proportional to the first gain factor.

31. A method according to claim 27, wherein the gain factors are calculated based on the historical data and the insulin secretion computational model.

32. A method according to claim 31, wherein the insulin secretion computational model is a pancreatic beta-cell computational model.

33. A method according to claim 27, wherein the gain factors are calculated based on historical measured blood glucose levels for the patient.

34. A method according to claim 27, wherein at least one of the gain factors is calculated by minimising a predicted insulin output level cost function based on the historical data over a predetermined period of time for a given glucose profile.

35. A method according to claim 34, wherein the predicted insulin output level cost function (J) is defined by:

$$J = \int_0^T U(t)\,dt - \left(\int_0^T SR_b(t)\,dt + \frac{CHO}{ICR}\right),$$

where T is the predetermined period of time, U(t) is the insulin output level of the insulin pump, $SR_b(t)$ is the minimum insulin rate, CHO is the amount of ingested carbohydrate, and ICR is the calculated insulin-to-carbohydrate ratio, which are adapted or derived from the historical data for the given glucose profile.

36. A method according to claim 27, further comprising calculating a set of gain factors determined from the historical data and a set of glucose profiles.

37. A computer readable medium comprising computer instructions stored thereon, which when executed on a processor or by processing logic, are adapted to perform the steps of:
   receiving a gain factor; the gain factor having been calculated based on historical data in relation to a patient;
   receiving data representative of a measured blood glucose level for the patient;
   applying the measured blood glucose level to an insulin secretion computational model to predict an insulin output level;
   applying the gain factor to the predicted insulin output level to determine a patient insulin deficiency level; and
   calculating a control signal for controlling the insulin output level of the insulin pump based on the patient insulin deficiency level;
   wherein the gain factor is arranged to be tuned to the patient by minimizing a predicted insulin output level cost function based on historical data of the patient.

38. A computer readable medium comprising computer instructions stored thereon, the computer instructions, which when executed on a processor or by processing logic, are adapted for determining one or more gain factors for use in controlling an apparatus according to claim 1 by calculating one or more gain factors based upon historical data in relation to a patient and entering the one or more gain factors via the user input of the apparatus;
   wherein the gain factor is arranged to be tuned to the patient by minimizing a predicted insulin output level cost function based on historical data of the patient.

* * * * *